(12) United States Patent
Zink et al.

(10) Patent No.: US 8,771,675 B2
(45) Date of Patent: Jul. 8, 2014

(54) PROBIOTIC STRAINS FOR PETS

(75) Inventors: Ralf Zink, Lagenfeld (DE); Roberto Reniero, Moyaux (FR); Florence Rochat, Montreux (CH); Christoph Cavadini, Corsier-sur-Vevey (CH); Thierry Von Der Weid, St.-Legier (CH); Eduardo Schiffrin, Crissier (CH); Jalil Benyacoub, Lausanne (CH); Virginie Rousseau, Pornic (FR); Pablo Perez, Lausanne (CH); Ruth Knorr, Bussy-les-Daours (FR)

(73) Assignee: Nestec S.A., Vevey (CH)

(*) Notice: Subject to any disclaimer, the term of this patent is extended or adjusted under 35 U.S.C. 154(b) by 1566 days.

(21) Appl. No.: 12/053,037

(22) Filed: Mar. 21, 2008

(65) Prior Publication Data

US 2008/0171106 A1  Jul. 17, 2008

Related U.S. Application Data

(60) Division of application No. 10/934,236, filed on Sep. 2, 2004, now Pat. No. 7,381,406, which is a continuation-in-part of application No. 10/296,070, filed on Apr. 18, 2003, now Pat. No. 7,189,390.

(30) Foreign Application Priority Data

May 25, 2000 (EP) .................................... 00201867
Apr. 25, 2001 (EP) .................................... 01201503

(51) Int. Cl.
| | |
|---|---|
| *A01N 63/00* | (2006.01) |
| *C12N 1/20* | (2006.01) |
| *A23K 1/18* | (2006.01) |
| *A23K 1/00* | (2006.01) |
| *C12R 1/23* | (2006.01) |
| *C12R 1/225* | (2006.01) |
| *A61K 35/74* | (2006.01) |
| *C12R 1/46* | (2006.01) |

(52) U.S. Cl.
CPC .............. *C12R 1/225* (2013.01); *A23K 1/1853* (2013.01); *A23K 1/009* (2013.01); *C12R 1/23* (2013.01); *A23K 1/1866* (2013.01); *A61K 35/747* (2013.01); *A61K 35/745* (2013.01); *Y10S 426/805* (2013.01); *C12R 1/46* (2013.01); *A61K 35/744* (2013.01)
USPC .......... 424/93.45; 426/61; 435/252.9; 426/805

(58) Field of Classification Search
None
See application file for complete search history.

(56) References Cited

U.S. PATENT DOCUMENTS

| | | | |
|---|---|---|---|
| 4,160,038 | A | 7/1979 | Groben et al. |
| 5,922,375 | A | 7/1999 | Luchansky et al. |
| 5,968,569 | A | 10/1999 | Cavadini et al. |
| 7,189,390 | B2 | 3/2007 | Cavadini et al. |

FOREIGN PATENT DOCUMENTS

| | | |
|---|---|---|
| WO | 96/08261 A1 | 3/1996 |
| WO | 99/17788 | 4/1999 |
| WO | 00/53202 | 9/2000 |

OTHER PUBLICATIONS

Patel et al., Journal of the American Society of Nephrology 13: Sept 2002 pp. 767A PUB476.*
Grovum et al., Br. J. Nutr. (1973)~vol. 30, pp. 377-.391.*
Balish, E., et al., "Nose, Throat, and Fecal Flora of Beagle Dogs Housed in "Locked" or "Open" Environments", Applied and Environmental Microbiology, Aug. 1977, vol. 34, No. 2, pp. 207-221.
Hartemink, R & Rombouts, F.M., "Comparison of media for the detection of *bifidobacteria*, *lactobacilli* and total anaerobes from faecal samples", Journal of Microbiological Methods, vol. 36 (1999) pp. 181-192.

* cited by examiner

*Primary Examiner* — Irene Marx
(74) *Attorney, Agent, or Firm* — K&L Gates LLP

(57) ABSTRACT

The present invention provides novel strains of probiotics for use in the gastrointestinal tract of a pet. The probiotics of the present invention are capable of fermenting starch to produce lactic acid and/or hydrogen peroxide anti-pathogenic metabolites. The present invention also provides a novel method for identifying the effectiveness of a pet probiotic in vitro. The method simulates the introduction of a probiotic candidate in the gastrointestinal tract of a pet and measures the anti-pathogenic effectiveness of the probiotic.

12 Claims, 6 Drawing Sheets

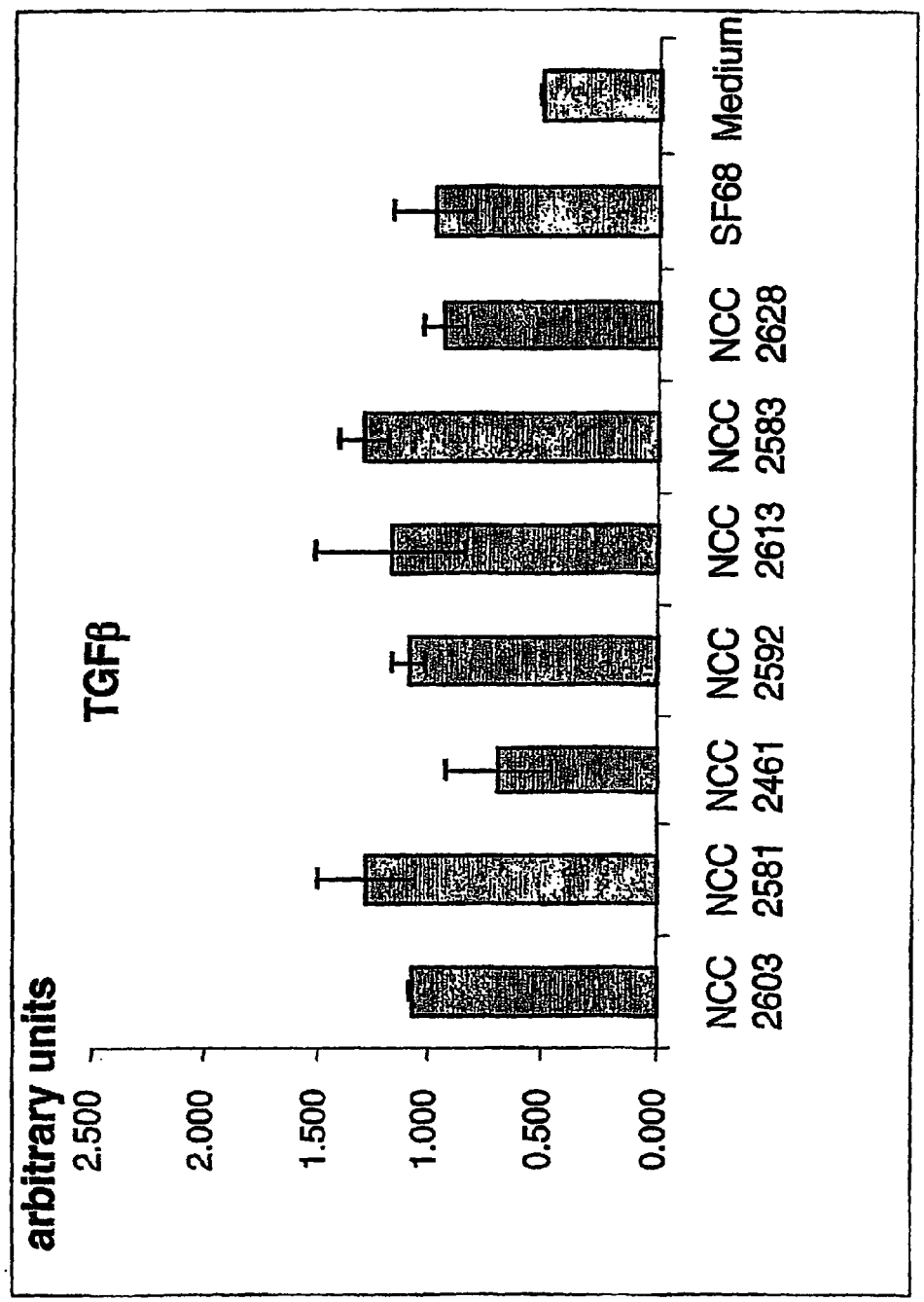

Storage of biomasses in sachets at 4°C and room temperature

PROBIOTIC STRAINS FOR PETS

PRIORITY CLAIM

This application is a divisional application of U.S. patent application Ser. No. 10/934,236 filed on Sep. 2, 2004, which is a continuation in part of U.S. patent application Ser. No. 10/296,070 filed on Nov. 21, 2002, which claims the benefit of European Patent Application Nos. 00201867.9 and 01201503.8 filed on May 25, 2000 and Apr. 25, 2001 respectively. The disclosures of which are incorporated herein by reference.

The present invention relates to novel lactic acid bacteria and particularly micro-organisms of the genera *Lactobacillus*, *Bifidobacterium* and *Streptococcus* (*Enterococcus*) that have been isolated and selected for their probiotic potential. The present invention also relates to their use in the preparation of pet food compositions intended to improve the health of pets and to compositions containing the same. Methods of maintaining or improving pet health through feeding a pet such micro-organisms are also provided.

BACKGROUND

The well-being of domestic animals is closely related to their feeding. Correct feeding should result in a fit and healthy pet. In addition to providing nutritional value, food composition influences the intestinal microflora equilibrium and may lead to or prevent gastrointestinal disorders. Therefore, knowledge on the gastro-intestinal tract and digestion processes of healthy animals is integral to the understanding of a practical feeding practice. As meat-eaters, cats and dogs are characterized by a short digestive tract and a rapid flow rate of the bolus of food.

Among the constituents of the gastrointestinal microflora of cats and dogs *Bacteroides* sp., *Clostridium* sp., Enterobacteriaceae, *Bifidobacterium* sp., *Lactobacillus* sp., *Streptococcus* sp., *Staphylococcus* sp. and yeasts can be recovered.

The number and composition of this endogenous flora tend to be rather stable, although age and, to a lesser degree, food may modify it. Gastric acidity, bile, intestinal peristalsis and local immunity are factors thought to be important in the regulation of bacterial flora in the small intestine of human beings and various other mammals.

Often canine and feline gastrointestinal disorders are linked to bacterial overgrowth and the production of enterotoxins produced by pathogenic bacteria.

During the last few years research has focused on some valuable strains of lactic acid bacteria and their potential use as probiotic agents. Probiotics are considered to be viable microbial preparations which promote mammalian health by preserving the natural microflora in the intestine. Probiotics are thought to attach to the intestinal mucosa, colonize the intestinal tract and thereby prevent attachment of harmful micro-organisms thereon. A prerequisite for their action resides in that they have to reach the gut's mucosa in a proper and viable form and especially do not get destroyed by the influence of the low pH prevailing in the stomach. In particular, the physiology of the digestive tract of cats and dogs differs from humans. For example, the average pH in the stomach is about 3.4 for dogs and 4.2 for cats.

Although U.S. Pat. No. 5,968,569 discloses the inclusion of a probiotic micro-organism in a pet food cereal, neither it, nor the remaining available art provides information concerning strains specifically intended for pet health.

Consequently, there is a need to provide novel bacterial strains that are particularly adapted for pets and that have been selected for their high probiotic properties beneficial for pet health and to incorporate these strains into a pet food composition.

SUMMARY

According to a first aspect of the invention, there is provided a novel probiotic micro-organism of lactic acid bacteria, selected for its ability to survive and colonize the gastrointestinal tract of a pet and to exert a beneficial probiotic activity on pet health.

The probiotic strain may be selected from lactobacilli, bifidobacteria or Enterococci.

The probiotic strain may be selected from the group consisting of *Lactobacillus reuteri*, *Lactobacillus acidophilus*, *Lactobacillus animalis*, *Lactobacillus ruminis*, *Lactobacillus johnsonii*, *Lactobacillus casei*, *Lactobacillus paracasei*, *Lactobacillus rhamnosus*, *Lactobacillus fermentum* and *Bifzdobacterium* spp., *Enterococcus faecium* and *Enterococcus* spp.

In an embodiment, the probiotic strain is selected from the group consisting of *Lactobacillus reuteri* (NCC2581; CNCM I-2448), *Lactobacillus reuteri* (NCC2592; CNCM I-2450), *Lactobacillus rhamnosus* (NCC2583; CNCM I-2449), *Lactobacillus reuteri* (NCC2603; CNCM I-2451), *Lactobacillus reuteri* (NCC2613; CNCM I-2452), *Lactobacillus acidophilus* (NCC2628; CNCM I-2453), *Bifidobacterium adolescentis* (e.g. NCC2627), *Biftdobacterium* sp. NCC2657 or *Enterococcus faecium* SF68 (NCIMB 10415).

The novel bacterial strain may be used in any amount from about 1.0E+04 to about 1.0E+12 cfu/animal and day and preferably from 1.0E+05 to about 1.0E+11 cfu/animal and day, most preferably from 1.0E+07 to 1.0E+10 cfu/animal and day.

In one aspect the invention relates to the use of the bacterial strain as described above and/or their supernatant of culture and/or their metabolites, for the preparation of a composition intended for the treatment and/or prophylaxis of disorders associated with the colonization of the gastrointestinal tract of pets by pathogenic micro-organisms. Unless the context clearly indicates otherwise, reference to "strain" should be understood to include its supernatant of culture and/or a metabolite thereof.

In another aspect, the invention relates to the use of the bacterial strain as described above and/or their supernatant of culture and/or a metabolite thereof, for the preparation of a composition intended for regulating the immune response of pets. By the term "regulating" the immune response, it is meant that the bacterial strains described above and/or their supernatant of culture and/or their metabolites have the capacity to either stimulate certain immune functions that are important to the pet's health or modulate other immune functions that could potentially be implicated in immune disorders, such as inflammation, allergy, etc. The stimulation or modulation of these immune functions can be achieved by using different combinations of the bacterial strains described above and/or their supernatant of culture and/or their metabolites.

The invention further provides a method of maintaining or improving the health of the gastrointestinal tract, the skin and/or coat system or the immune system of a pet comprising the step of feeding a pet a pet food composition containing at least one isolated strain as described above.

In addition, the invention provides a method for the treatment and/or prophylaxis of disorders associated with the colonization of the gastrointestinal tract of pets by pathogenic micro-organisms, comprising the step of feeding a pet a pet food composition containing at least one isolated strain according to the present invention.

The invention also provides a method of regulating the immune response in pets, comprising the step of feeding a pet a pet food composition containing at least one isolated strain according to the present invention.

The invention also provides a method of ameliorating or reducing the effects of ageing in a pet comprising the step of feeding a pet a pet food composition containing at least one isolated strain according to the present invention.

These selected micro-organisms have a particular beneficial impact on pets in their gastrointestinal tract, on their skin and/or coat, on their immune system, and on the effects of ageing.

They have a particular beneficial impact on intestinal pathogens such as strains *Salmonella typhimurium, Escherichia coli, Shigella dysenteriaea* or other pathogenic enterobacterieceae colonizing pets or parasites such as helminths (*Toxocara* spp.), protozoan (*Cryptosporidium* spp, *Giardia* spp., *Pentatrichomonas hominis, Entamoeba histolydca, Toxoplasma gondii*, . . . ) or yeasts.

Combined with food, these micro-organisms particularly exert their probiotic beneficial effects on palatability, digestion and gut health, immune function and sanitary conditions, the latter by way of contributing to a reduction of fecal volume and at least a partial deodorization of canine faeces. Thus, according to a second aspect of the invention, a pet food composition comprises a micro-organism having high probiotic activity in pets and being capable of surviving and colonizing the gastrointestinal tract of a pet ingesting it.

Accordingly, the invention relates to a pet food composition intended for the health of the gastrointestinal tract of pets, containing at least one probiotic strain isolated as described above and/or a supernatant of its culture and/or a metabolite thereof, associated with an ingestible support or a pharmaceutical matrix.

Also, the invention relates to a pet food composition intended for the regulation of the immune response of pets, containing at least one isolated strain as described above and/or a supernatant of its culture and/or a metabolite thereof, associated with an ingestible support or a pharmaceutical matrix.

Also, the invention relates to a pet food composition intended for ameliorating or reducing the effects of ageing in pets, containing at least one isolated strain as described above and/or a supernatant of its culture and/or a metabolite thereof, associated with an ingestible support or a pharmaceutical matrix.

Finally, the invention relates to a pet food composition intended for the health of the skin and/or coat of pets, containing at least one isolated strain as described above and/or a supernatant of its culture and/or a metabolite thereof, associated with an ingestible support or a pharmaceutical matrix.

In an embodiment, the ingestible support comprises a nutritionally balanced pet food composition. The said composition preferably contains sufficient amount of the isolated strain, it supernatant of culture and/or a metabolite thereof, to be effective in providing the said prophylactic effect when the composition is fed to a pet as a complete meal.

In a further embodiment, a starch fermenting probiotic capable of colonizing and surviving in a gastrointestinal tract of a pet is provided. The starch fermenting probiotic may produce an anti-pathogenic metabolite selected from the group consisting of lactic acid, acetic acid, citric acid, pyruvic acid, hydrogen peroxide, and combinations thereof. In a further embodiment, the present invention provides a probiotic capable of colonizing and surviving in a gastrointestinal tract of a pet wherein the probiotic produces hydrogen peroxide.

In another embodiment, a method for identifying an effective pet probiotic is provided. The method includes providing a probiotic and exposing the probiotic to a gastric juice. A model of a pet small intestine is provided and the probiotic and a pathogen are introduced into the model. The method further includes measuring the amount of anti-pathogenic metabolite produced by the probiotic.

Additional features and advantages are described herein, and will be apparent from the following Detailed Description and the figures.

DETAILED DESCRIPTION

Figure 1:
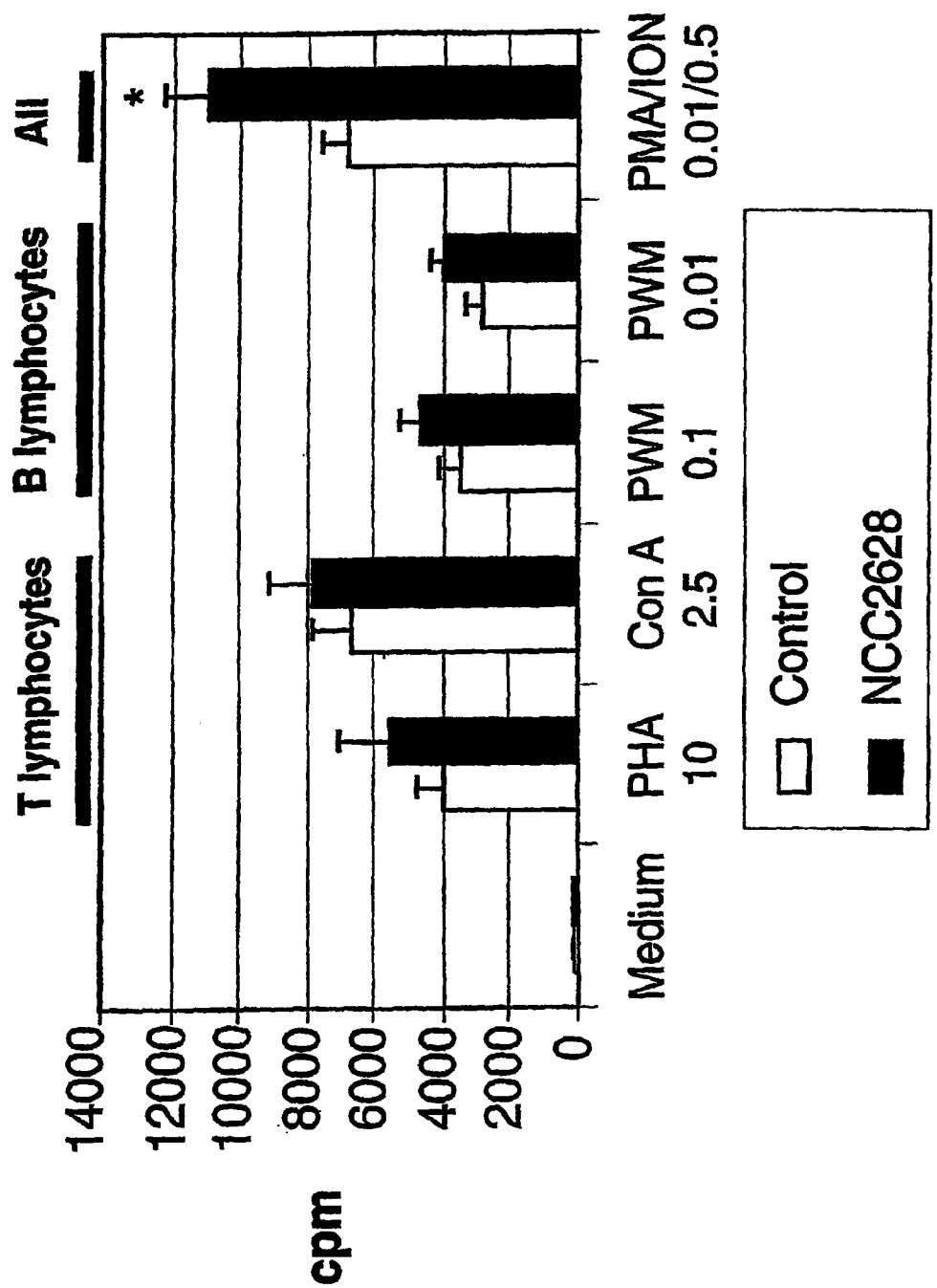
FIG. 1 is a graph showing lymphocyte proliferation of canine peripheral blood mononuclear cells upon stimulation with mitogens or phorbol esters.

Within the following description, the abbreviation cfu ("colony-forming-unit") designates the number of bacterial cells as revealed by microbiological counts on agar plates.

Moreover, "NCC" designates Nestle Culture Collection (Nestle Research Center, Vers-chez-les-Blanc, Lausanne, Switzerland).

With respect to the first object of the present invention, 20 lactobacilli and 18 bifidobacteria isolated from cat and dog faeces, were screened and selected with regard to their technological and physiological parameters.

A first screening for potential probiotic applications was performed in-vitro (see examples 1 and 2): growth characteristics, tolerance to gastric acidity at different pHs and different concentrations of biliary salts present in the duodenum likely to be found in cats and dogs.

Furthermore, the good survival of freeze-dried cells in two different cryoprotective media was clearly demonstrated at 4° C. and 20° C. as indicated by an accelerated storage test.

These strains can be characterized by short generation times, high counts (more than 1.0E+08 cfu/ml) during their stationary phase and stability in high numbers at 8 and 24 h post-inoculation, stability to freeze-drying followed by either storage-conditions, resistance to physiological bile concentrations found in the duodenum (2% bile) and their low inhibition when grown in presence of up to 4% bile. Furthermore, results from DNA analyses were taken into account to select bacteria representative of the investigated diversity.

The strains intended for cat and dog health can grow up to at least 1.0E+06 cfu/ml in the presence of up to 2.0% bile salts. The strains can also grow up to at least 1.0E+06 cfu/ml after about 2 hours at a pH-range from about 3.4 to about 4.2.

The bacterial strains according to the invention may be selected from the group consisting of *Lactobacillus reuteri, Lactobacillus acidophilus, Lactobacillus animalis, Lactobacillus ruminis, Lactobacillus johnsonu, Lactobacillus casei, Lactobacillus paracasei, Lactobacillus rhamnosus, Lactobacillus fermentum, Bifidobacterium* sp., *Enterococcus faecium, Enterococcus* sp.

The following strains *Lactobacillus reuteri* NCC2581, *Lactobacillus rhanutosus* NCC2583, *Lactobacillus reuteri* NCC2592, *Lactobacillus reuteri* NCC2603, *Lactobacillus reuteri* NCC2613, and *Lactobacillus acidophilus* NCC2628 were deposited by the way of an example under the Budapest Treaty, at the Collection Nationale de Culture de Micro-organismes, 25 rue du docteur Roux, 75724 Paris, France, on Apr. 19, 2000, under the following references CNCM I-2448, CNCM I-2449, CNCM I-2450, CNCM I-2451, CNCM I-2452 and CNCM I-2453, respectively. All restrictions as to the availability of these deposits will be withdrawn upon first publication of this application or another application which claims benefit of priority to this application.

*Lactobacillus acidophilus* NCC 2766 (CNCM I-3848), *Lactobacillus acidophilus* NCC 2775 (CNCM I-3851), *Lactobacillus acidophilus* NCC 2628 (CNCM I-2453), *Lactobacillus johnsonii* NCC 2777 (CNCM I-3852), *Lactobacillus johnsonii* NCC 2767 (CNCM I-3849), *Lactobacillus johnsonii* NCC 2774 (CNCM I-3850), and *Lactobacillus salivarius* NCC 2586 (CNCM I-3847) were all deposited on Oct. 16, 2007 under the Budapest Treaty at the Collection Nationale de Culture de Micro-organismes, 25 rue du docteur Roux, 75724 Paris, France. All restrictions as to the availability of these deposits will be withdrawn upon first publication of this application or another application which claims benefit of priority to this application.

Biochemical Characterization of the Selected Strains
*Lactobacillus reuteri* CNCM I-2448
Gram positive micro-organism, non-motile, non-sporing
Fairly short and thick rodlets
Microaerophilic micro-organism with heterofermentative metabolism, production of L (+) and D (−) lactic acid
Catalase (−), production of $CO_2$ from glucose, hydrolysis of arginine =NH3 production
Growth with 5% and 10% NaCl
Fermentation of sugars: L-arabinose, galactose, D-glucose, lactose, saccharose, D-raffinose

*Lactobacillus rhamnosus* CNCM I-2449
Gram positive micro-organism, non-motile, non-sporing
Fairly short and thick rodlets
Microaerophilic micro-organism with heterofermentative metabolism, production of L (+) lactic acid.
Catalase (−),
Fermentation of all sugars typical for *Lb. rhamnosus*

*Lactobacillus reuteri* CNCM I-2450
Gram positive micro-organism, non-motile, non-sporing
Fairly short and thick rodlets
Microaerophilic micro-organism with heterofermentative metabolism, production of L (+) and D (−) lactic acid
Catalase (−), production of $CO_2$ from glucose, hydrolysis of arginine =NH3 production
Growth with 5% and 10% NaCl
Fermentation of sugars: L-arabinose, galactose, D-glucose, D-xylose, lactose, saccharose, D-raffinose

*Lactobacillus reuteri* CNCM I-2451
Gram positive micro-organism, non-motile, non-sporing
Fairly short and thick rodlets
Microaerophilic micro-organism with heterofermentative metabolism, production of L (+) and D (−) lactic acid
Catalase (−), production of $CO_2$ from glucose, hydrolysis of arginine =NH3 production
Growth with 5% and 10% NaCl
Fermentation of all sugars which are typical for *Lb. reuteri*

*Lactobacillus reuteri* CNCM I-2452
Gram positive micro-organism, non-motile, non-sporing
Fairly short and thick rodlets
Microaerophilic micro-organism with heterofermentative metabolism, production of L (+) and D (−) lactic acid
Catalase (−), production of $CO_2$ from glucose, hydrolysis of arginine =NH3 production
Growth with 5% and 10% NaCl
Fermentation of sugars: L-arabinose, D-glucose, lactose, saccharose, D-raffinose

*Lactobacillus reuteri* CNCM I-2453
Gram positive micro-organism, non-motile, non-sporing
Fairly short and thick rodlets
Microaerophilic micro-organism with homofermentative metabolism, production of L (+) and D (−) lactic acid
Catalase (−),
Fermentation of sugars: D-glucose, lactose, saccharose, D-raffinose Three lactobacilli isolated from cats (NCC2581, NCC2592, NCC2583), three lactobacilli from dogs (NCC2603, NCC2613, NCC2628), one bifidobacteria from cats (NCC2627) and one bifidobacteria from dogs (NCC2657) were further tested for their probiotic potential activity in pets (see examples 3 and 4).

In another embodiment, the present invention relates to the use of bacterial strains as described above, for the preparation of a food composition capable of improving or maintaining pet health.

They can be used in their viable form, inactivated form, as a supernatant of a culture or fractions thereof, e.g. cell walls, peptidoglycan, cytoplasm, purified proteins, functional metabolites, bioactive molecules.

They are preferably used in an amount of from about 1.0E+04 cfu/g to about 1.0E+11 cfu/g and preferably from 1.0E+05 cfu/g to about 1.0E+10 cfu/g, most preferably from 1.0E+06 cfu/g to 1.0E+09 cfu/g.

In a preferred embodiment, they may be used as dietary adjuncts so as to improve pet food quality and may be included in an amount of from about 1.0E+04 cfu/g to about 1.0E+11 cfu/g. As dietary adjuncts, they may be encapsulated or may be provided in powder form and packaged in conjunction with or separately from a main meal, be it wet or dry. By way of example, a powder containing selected micro-organisms according to the invention, or components or moieties of the supernatant of their cultures or selected metabolites, may be packed in sachets in a powder form or in a gel or lipid or other suitable carrier. These separately packaged units may be provided together with a main meal or in multi-unit packs for use with a main meal or treat, according to user instructions. In another example, the probiotic strains may be provided in a multi-chamber packaging unit together with a second ingestible component, for example a wet or medium moisture content chunky meal or a meal-sized batch of dried kibbles in a flexible pouch configuration. A first chamber in the pouch would contain the probiotic strain and a second, separate sealed chamber the second ingestible component.

These selected micro-organisms have a particular beneficial impact in pets on their gastrointestinal tract, on their skin and/or coat, on their immune system, on dental or oral health, on their bones and on the effects of ageing.

They are also found to improve palatability of food, digestion, immune function and sanitary conditions (reduction of fecal volume and partial deodorization of canine faeces) in pets.

The present invention also relates to a pet food composition for improving or maintaining the health of pets containing at least one probiotic strain having the above traits, associated with an ingestible support or a pharmaceutical matrix.

At least one bacterial strain having the above traits and/or its supernatant of culture or a fraction thereof and/or its metabolites may be administered to the pet as a supplement to its normal diet or as a component of a nutritionally complete pet food.

The nutritionally complete pet food composition according to the invention may be in powdered, dried form or a wet, chilled or shelf stable pet food product. These pet foods may be produced by ways known in the art provided that where micro-organism activity is desired, care is taken to ensure survival of the micro-organism. Apart from the bacteria strains and/or its fermented medium, these pet foods may include any one or more of a starch source, a protein source and lipid source.

Suitable starch sources are, for example, grains and legumes such as corn, rice, wheat, barley, oats, soy, and mixtures of these.

Suitable protein sources may be selected from any suitable animal or vegetable protein source; for example meat and meal, poultry meal, fish meal, soy protein concentrates, milk proteins, gluten, and the like. For elderly animals, it is preferred for the protein source to contain a high quality protein.

Suitable lipid sources include meats, animal fats and vegetable fats.

The choice of the starch, protein and lipid sources will be largely determined by the nutritional needs of the animal, palatability considerations, and the type of product applied. For elderly pets, the pet food preferably contains proportionally less fat than pet foods for younger pets. Furthermore, the starch sources may include one or more of rice, barley; wheat and corn.

Further, various other ingredients, for example, sugar, salt, spices, seasonings, vitamins, minerals, flavoring agents, fats and the like may also be incorporated into the pet food as desired.

For dried pet foods a suitable process is extrusion cooking, although baking and other suitable processes may be used. When extrusion cooked, the dried pet food is usually provided in the form of a kibble. If a prebiotic carbohydrate is used, the prebiotic may be mixed with the other ingredients of the dried pet food prior to processing. A suitable process is described in European patent application No 0850569; the disclosure of which is incorporated by reference. If a probiotic micro-organism is used and activity is desired in the final product, the organism is best coated onto or filled into the dried pet food. A suitable process is described in European patent application No 0862863; the disclosure of which is incorporated by reference. Where survival of the micro-organism is not required, it may be added to the pre-extrusion mix, as may the supernatant of its culture or metabolite, as desired.

For wet foods, the processes described in U.S. Pat. Nos. 4,781,939 and 5,132,137 may be used to produce simulated meat products. The disclosures of these patents are incorporated by reference. Other procedures for producing chunk type products may also be used; for example cooking in a steam oven. Alternatively, loaf type products may be produced by emulsifying a suitable meat material to produce a meat emulsion, adding a suitable gelling agent, and heating the meat emulsion prior to filling into cans or other containers. As in the case of producing dried pet foods, where survival of the probiotic species chosen is not essential, it may be added to the feed mix prior to cooking or heating, or at any appropriate or convenient stage in the production process.

The amount of prebiotic in the pet food is preferably less than about 20% by weight and further preferably less than about 10% by weight. For example, the prebiotic may comprise from about 0.1% to about 5% by weight of the pet food. For pet foods which use chicory as the prebiotic, the chicory may be included to comprise from about 0.5% to about 10% by weight of the feed mixture; more preferably from about 1% to about 5% by weight.

The pet foods may contain other active agents such as long chain fatty acids. Suitable long chain fatty acids include alpha-linoleic acid, gamma-linoleic acid, linoleic acid, eicosapentanoic acid, and docosahexanoic acid. Fish oils are a suitable source of eicosapentanoic acids and docosahexanoic acid. Borage oil, blackcurrant seed oil and evening primrose oil are suitable sources of gamma-linoleic acid. Safflower oils, sunflower oils, corn oils and soy bean oils are suitable sources of linoleic acid.

If necessary, the pet foods are supplemented with minerals and vitamins so that they are nutritionally complete.

Furthermore, if desired, the bacteria strain may be encapsulated; for example in a sugar matrix, fat matrix or polysaccharide matrix. It may also be coated as described in EP 862 863.

The novel probiotic strain is preferably used so that the pet food to preferably contains about 1.0E+04 to about 1.0E+10 cells of the probiotic micro-organism per gram of the pet food; more preferably about 1.0E+06 to about 1.0E+08 cells of probiotic micro-organism per gram. The pet food may contain about 0.005% to about 10% by weight of the mixture of the probiotic micro-organism. It preferably contains about 0.02% to about 6% by weight and most preferably about 1% to about 6% by weight.

The amount of pet food to be consumed by the pet to obtain a beneficial effect will depend on the size or the pet, the type of pet, and age of the pet. However, an amount of the pet food to provide a daily amount of about 1.0E+03-1.0E+14 cfu of at least one lactic acid bacteria strain and/or the equivalent fermentation medium, would usually be adequate. Preferably about 1.0E+09 to 1.0E+11 cfu/day for dogs or 1.0E+07 to 1.0E+10 cfu/day for cats are administered.

The composition according to the invention has a high probiotic activity and/or is found to be particularly effective for improving and/or maintaining healthy digestive function in pets, and improving and maintaining the gastrointestinal tract, skin and/or coat, and/or immune system, health of pets. This composition has also a beneficial impact on effects of ageing in cats and dogs.

In a further embodiment, the present invention provides a starch fermenting probiotic capable of colonizing and surviving in a gastrointestinal tract of a pet. The strains in this embodiment selected for application as pet probiotics are of canine or feline origin and comprise the *Lactobacillus acidophilus* group (*L. acidophilus, L. johnsonii*) and *L. salivarius*. The strains were identified by various molecular methods. Table A lists the identification and origin of the strains. All strains are different from each other. The dog strains were isolated from different dogs whereas the cat strains are derived from one cat but comprise different species.

TABLE A

Identification (patterns of molecular methods) and origin of selected strains

| NCC | *Lactobacillus* species | Ribo-type | SDS-PAGE | AFLP | PFGE | REP-PCR | | Origin |
|---|---|---|---|---|---|---|---|---|
| 2766 | *Acidophilus* | A2a | — | A4 | — | — | dog7 | Amiens |
| 2775 | *Acidophilus* | A1a | — | A2a | — | — | dog9 | Amiens |
| 2628 | *Acidophilus* | A2b | — | A5 | — | — | dog061 | St. Joseph |

TABLE A-continued

Identification (patterns of molecular methods) and origin of selected strains

| NCC | Lactobacillus species | Ribo-type | SDS-PAGE | AFLP | PFGE | REP-PCR | Origin | |
|---|---|---|---|---|---|---|---|---|
| 2777 | Johnsonii | J1 | — | J2a | J2 | J2 | dog582 | St. Joseph |
| 2767 | Johnsonii | J1 | — | J1d | J1 | J1 | dog478 | St. Joseph |
| 2774 | Johnsonii | J1 | — | J2b | J2 | J2 | cat403 | St. Joseph |
| 2586 | Salivarius | R1a | R1 | — | — | — | cat403 | St. Joseph |

Lactobacilli are reported to be a part of the natural microflora of healthy dogs; they were found all along the gastro-intestinal tract, with their numbers increasing from stomach to the colon (from log 5 to log 11 CFU/g) and in the faeces. Young dogs had higher counts of lactobacilli in the large intestine than older dogs. Studies which discriminated between lactobacilli species showed variations for individual dogs as well as dependency of the microbial patterns and numbers on age, or location in the intestinal tract. Some studies identified the species *L. salivarius* and *L. acidophilus*, with the latter group probably including *L. johnsonii* due to the limited differentiation techniques and/or taxonomy used at the time of the studies. Besides from being a part of the gut microflora of dogs, lactobacilli were also found in ears, nose, throat and dental plaque of dogs. Lactobacilli were also found in the duodenum and feces of healthy cats.

These two reasons—(1) that lactobacilli are a part of the natural canine and feline microflora and (2) that the specific strains were isolated from healthy dogs and cats with a balanced, well-working microflora—speak for the safety of the establishment of these strains in other dogs and cats. The strains are likely to resume their natural function when reintroduced to the animal. The probiotic population will become a (transient) part of the natural microflora and is likely to be regulated.

Finally, *Lactobacillus acidophilus* strains (interpreted as group) are GRAS and allowed in the United States as feed additive according to the AAFCO guidelines. Only rare cases of systemic infections with lactobacilli have been reported, with serious underlying conditions in nearly all of the patients. Furthermore, although the yearly consumption of probiotic products containing lactobacilli has increased during the last decade, the incidence of lactobacillemia has not increased. Thus the risk for humans of serious infection by probiotic lactobacilli is very low. A study in dogs, which investigated the translocation of intestinally derived bacteria, did not identify lactobacilli in the blood. In the mesenteric lymph nodes, a *Lactobacillus* sp. was found in one out of 50 healthy dogs. The significance of the latter finding, whether it just enhances immune stimulation or increases the danger of systemic infection, is still to be elucidated.

The fact that the strains were isolated from dogs and cats not only demonstrates their adaptation to the animal but also their adaptation to the pet food and its intestinal metabolites. Experimentation demonstrated that the selected strains will most likely be metabolically active in the small intestine, the major site for immune modulation as well as interaction with pathogens. The in vivo conditions in a canine small intestinal were simulated in an in vitro model supplemented with pet food. In this model, the physiologically most active strains were the *L. acidophilus* and *L. johnsonii* strains. These strains were the only ones being able to ferment starch, the main carbon source in the pet food. Some *L. salivarius* strains were also physiologically active but to a lesser extent (measured as bactericidal activity, acidification, and peroxide production).

Not wishing to be bond by any particular theory, it is believed that these non starch-fermenting strains were most likely supplied with the required sugar sources by enzymatic starch-degrading activities.

The selected strains were stable under gastric conditions (less than one log loss) (see Table B). Under small intestinal conditions, the *L. johnsonii* strains NCC2777, NCC2767, and NCC2774 were less stable than the other strains (see Table C). This can be explained by their high metabolic activity that leads to production of peroxide and self-inhibition.

TABLE B pH stability of selected strains

| NCC | delta lg CFU/ml after 10 min at pH 2.6 | S.D. | delta lg CFU/ml after 60 min at pH 3.4 | S.D. |
|---|---|---|---|---|
| 2766 | −0.5 | 0.1 | −0.2 | 0.2 |
| 2775 | −0.1 | 0.0 | −0.1 | 0.0 |
| 2628 | −0.1 | 0.2 | 0.0 | 0.1 |
| 2777 | −0.3 | 0.2 | −0.1 | 0.3 |
| 2767 | −0.3 | 0.1 | −0.8 | 0.1 |
| 2774 | −0.1 | 0.0 | −0.1 | 0.0 |
| 2586 | −0.4 | 0.1 | −0.6 | 0.1 |

S.D. is the standard deviation (four experiments per sample).

TABLE C stability of selected strains under small intestinal conditions

| NCC | loss log CFU/ml | S.D. |
|---|---|---|
| 2766 | −0.3 | 0.1 |
| 2775 | 0.2 | 0.5 |
| 2628 | −0.1 | 0.3 |
| 2777 | −2.6 | 0.6 |
| 2767 | −2.0 | 1.0 |
| 2774 | −1.4 | 0.6 |
| 2586 | −0.6 | 1.0 |

S.D. is the standard deviation (four experiments per sample).

The selected strains produce anti-pathogenic metabolites that exhibit high antimicrobial activity under small intestinal conditions. The anti-pathogenic metabolites were actually able to inactivate the tested pathogens (ETEC, *E. coli* (pathogenic canine isolate), *Salmonella typhimurium, Shigella dysenteriae*) and combinations thereof rather than just inhibiting their growth. The anti-pathogenic metabolites or antimicrobial principles were identified as lactic acid production (up to 90 mM) and lowering of the pH (down to 4.5-5.0) for the *L. acidophilus* strains, and production of peroxide (up to 4.5 mM) for the *L. johnsonii* strains. The *L. salivarius* strains were antimicrobially active by combining these two principles and possibly an additional antimicrobial mechanism. In an embodiment, the metabolite lowered the pH of the gastrointestinal tract locally to a range from about 4.5 to about 5.5. Table D shows the results for the physiological and antimicrobial activity of the selected strains in the canine small intestinal model.

Most strains demonstrated excellent stability in conditions simulating the canine stomach, losing less than one log colony-forming-unit (CFU)/mL. Strains typed *L. acidophilus* were stable in conditions mimicking the canine small intestine, and effectively inactivated pathogenic strains of *E. coli* of both human and canine origin. In an embodiment, these strains utilized starch from the dog food, and produced large amounts of lactic acid (70-90 mM) that lowered the pH to 4.5. In an embodiment, strains typed *L. johnsonii* also utilized the starch in dog food and effectively inactivated *E. coli* of both human and canine origin, but were less stable in conditions mimicking the small intestine due to self-inactivation caused by high hydrogen peroxide production (3-4 mM). In a further embodiment, strains of *L. johnsonii* produced less lactic acid (10-17 mM) and had less effect on pH (5.2). *L. salivarius* strains were less effective against pathogens, possibly because they did not utilize the starch from the dog food, and seemed to combine both lactic acid and hydrogen peroxide as antimicrobial agents.

TABLE D

Physiological activity of selected strains in the canine small intestinal model, measured as final pH, lactic acid and peroxide production, and inactivation of ETEC

| NCC | ETEC delta log CFU/ml | SD | final pH | SD | lactic acid mM | SD | $H_2O_2$ mM | SD |
|---|---|---|---|---|---|---|---|---|
| 2766 | −1.9 | 0.5 | 4.5 | 0.0 | 87 | 6 | 0.7 | 0.2 |
| 2775 | −1.9 | 0.9 | 4.5 | 0.0 | 82 | 18 | 0.1 | 0.0 |
| 2628 | −1.1 | 0.4 | 4.5 | 0.0 | 72 | 28 | 0.5 | 0.0 |
| 2777 | −2.8 | 0.3 | 5.4 | 0.1 | 10 | 2 | 4.1 | 0.6 |
| 2767 | −2.0 | 1.0 | 5.0 | 0.1 | 17 | 3 | 3.2 | 0.5 |
| 2774 | −1.7 | 1.1 | 5.3 | 0.2 | 14 | 0 | 3.5 | 0.4 |
| 2586 | −0.3 | 0.2 | 4.8 | 0.2 | 44 | 12 | not found | |
| ETEC | 5.6 | 0.5 | 5.8 | 0.2 | 2 | 2 | not found | |

SD is the standard deviation (2-4 experiments per sample were performed)

Inhibition of enteropathogens, such as enteropathogenic *E. coli*, *Salmonella typhimurium*, and *Shigella* sp., is generally observed at pH values below 5.0. The fact that these pH values can actually be encountered in the canine small intestine was confirmed by data from several publications, mainly from studies with fistulated dogs. The second major anti-pathogenic metabolite, hydrogen peroxide, has been shown to inhibit a large variety of bacteria, such as *Pseudomonas fragi* at 0.2 mM, *S. aureus* at 0.6 mM, and *S. typhimurium* at 0.4 mM. In a study performed by Hyslop, *E. coli* was killed by 0.5 mM $H_2O_2$, which agrees with the results of the present invention.

One of the selected strains, NCC2628, has been the subject of further studies on antipathogenic activity: in an in vitro experiment, the supernatant of NCC2628 inhibited proliferation of *Giardia intestinalis* trophozoites. Also, in a mouse model, strain NCC2628 has been shown to prevent translocation of *Salmonella typhimurium* into deeper tissue.

Figure 3:
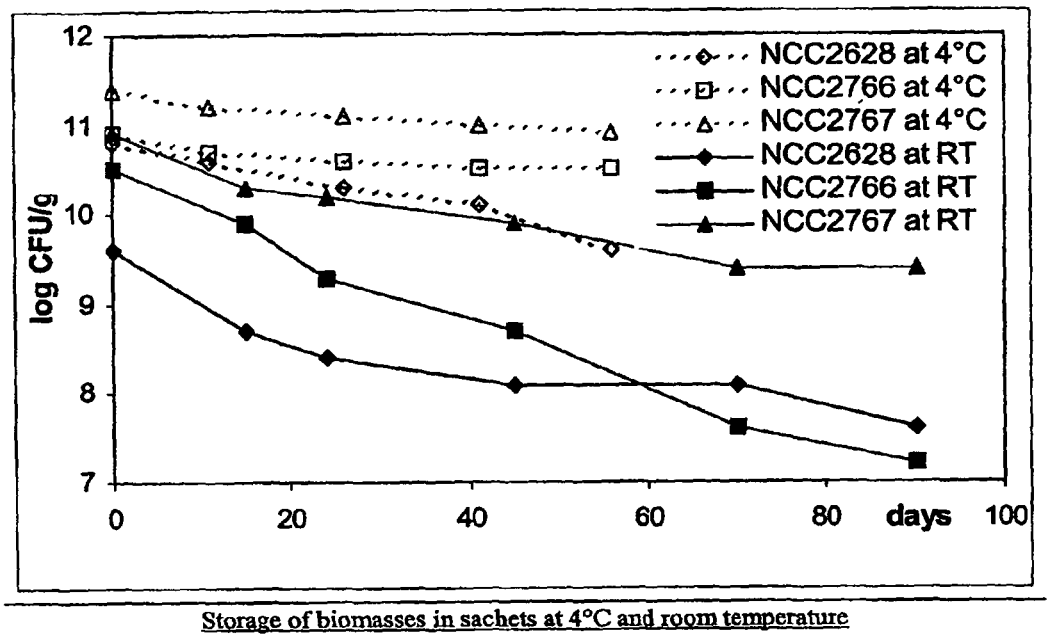
FIG. 3 is a graph showing the stability of biomasses stored in sachets over time.

The delivery of NCC2767, NCC2766, and NCC2628 is performed in a drug application mode. For this purpose, freeze-dried biomasses were produced. To produce a canine probiotic cocktail, the biomasses were mixed and filled in sachets (1 g of mixed biomasses with about log 10 CFU/g of each strain). All other strains have so far only been handled under laboratory conditions. The cocktail as well as the individual strains are stable at −40° C. for at least 4.5 months and at 4° C. for 8 weeks (highest loss about 1 log CFU/g for NCC2628 at 4° C.) as shown in FIG. 3. During storage for 90 days at room temperature, the cocktail lost about 1 log CFU/g, with different survival rates for the individual strains. The storage data are shown in FIG. 3.

Figure 4:
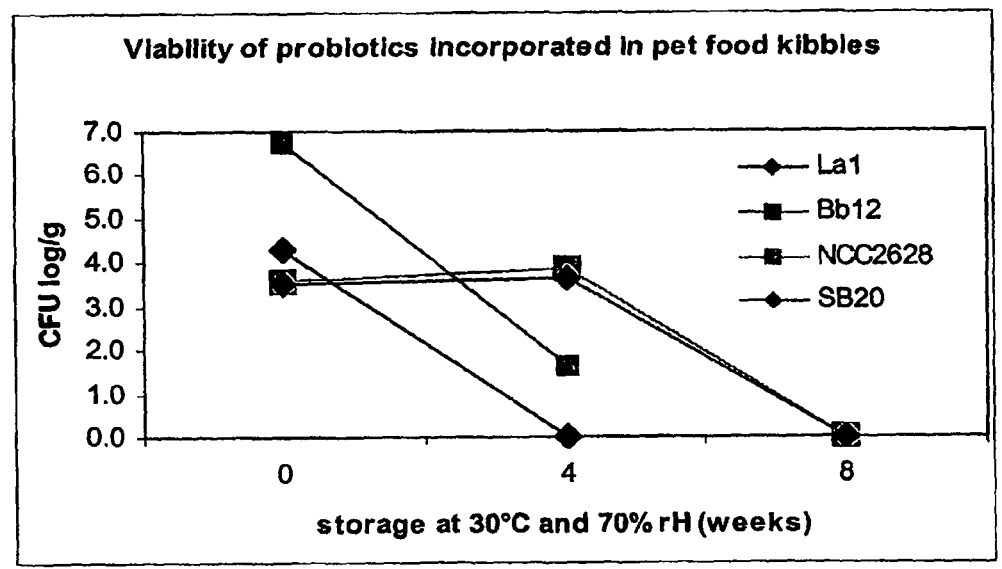
FIG. 4 is a graph showing the viability of stored probiotics incorporated in pet food over time.

Incorporation of NCC2628 in pet food kibbles and forced storage at 30° C. and 70% rH resulted in stability for 4 weeks but complete loss of viability after 8 weeks as shown in FIG. 4. Nevertheless, NCC2628 was more stable than two other organisms (La1 and Bb12) tested in this system.

The canine cocktail was applied in a clinical study treating dogs with chronic diarrhea. The dogs were divided into 3 groups (IBD, Dietary Hypersensitivity, ARD) according to the intestinal histopathological assessment. The hypotheses was (1) that the three groups could be differentiated by cytokine mRNA expression and immunohistochemistry and (2) that probiotics would have an influence on immune response & recovery/relapse. In order to select appropriate strains for this study, several pet strains were tested for their in vitro stimulation of canine peripheral mononuclear cells and chosen for their regulatory (IL-10: NCC2628, NCC2766) and stimulatory (IL-12: NCC2767) cytokine expression profiles.

The in vitro data, demonstrates that the selected strains are likely to exert probiotic activity in vivo, in dogs and cats. The strains will survive gastric transit and be physiologically active in the small intestine which means they will compete for nutrients and produce antimicrobial substances and/or anti-pathogenic metabolites with activity against a wide range of pathogens. Furthermore the strains might have a regulatory and/or immune stimulating effect.

In a further embodiment, the present invention provides a method for identifying an effective pet probiotic. The method includes providing a probiotic, exposing the probiotic to a gastric juice in order to assess the probiotic resistance thereto. The method also includes providing a model of a pet small intestine, introducing the probiotic and a pathogen into the model, and measuring the amount of an anti-pathogenic metabolite produced by the probiotic.

Probiotics are live micro-organisms that, when ingested as a feed supplement in sufficient numbers, beneficially affect the gastrointestinal balance, going far beyond the conventional nutritional effect. The most commonly used probiotics are those bacteria producing lactic acid (lactic acid bacteria; LAB) such as lactobacilli and bifidobacteria, and a variety of health-related effects have been observed for LAB in human and farm animal studies. These include preventative health-effects, since maintenance of a balanced gastrointestinal microflora can competitively exclude pathogens, and probiotics also have a modulatory effect on the immune system. Probiotics have also been used for the treatment of gastrointestinal disorders including diarrhea.

Despite all these findings in other species, known uses of probiotics in companion animals is minimal at best. There are few studies demonstrating actual health benefits in dogs. This may be because studies in vivo are costly, time consuming, technically demanding, and can be ethically controversial (e.g. challenge tests). Efficacy has been studied by inoculation of a pathogen along with a canine probiotic into a germ-free rodent model, however, extrapolation to the situation in vivo is difficult since this assay does not take into account the conditions in the canine gastrointestinal tract. However, some health benefits of probiotics can be measured non-invasively, e.g. positive effects on the immune system by measuring immune markers in the saliva, feces and serum. A significantly improved specific immune response to vaccination and increased levels of secretory IgA were reported in young dogs following supplementation with a probiotic from weaning to one year of age. These findings suggest that probiotics may be beneficial for companion animal species, particularly during periods of stress or infection.

The present invention advantageously provides a method that reduces the requirement for studies in vivo. Known multi-compartment models of the human gastrointestinal tract have been constructed to allow the screening and study of potentially probiotic strains. The small intestine is the major site for nutrient absorption, immune stimulation and pathogen activity and is therefore the target for probiotic interaction. The present invention provides a simulated pet small intestine for the study of likely probiotic efficacy in pets.

The present method advantageously provides a rapid, high-throughput in vitro screening system to identify candidate canine-specific probiotics, originating from the bacteria present in the feces of healthy dogs. The method identifies strains that demonstrate resistance against conditions mimicking those found in the canine stomach and small intestine. In addition, the method screens for anti-pathogenic activity and functional properties such as the utilization of available substrates and the production of anti-microbial metabolites. The method simulates the canine stomach and small intestine and allows screening for resistance against these conditions, anti-pathogenic activity, and functional properties such as utilization of available substrates and production of anti-pathogenic metabolites.

In an embodiment, the method includes obtaining fresh feces from healthy dogs and viable lactobacilli cultured in MRS (De Man Rogosa and Sharpe) broth at 37° C., anaerobically. Cultures showing different morphology on MRS and HHD (Homofermentative-Heterofermentative Differentiation) agar were separated, and different strains characterized by standard biochemical and molecular biological techniques (SDS-PAGE; AFLP; PFGE; 16S rRNA sequencing; Ribotyping). Cultures were maintained by subculturing every two weeks in MRS and storage at 4° C. Permanent stock cultures were maintained by storing at −80° C. in cryoprotective medium (containing 30% glycerol and 50% MRS).

In an embodiment, the method includes obtaining or otherwise providing a pathogen. In a further embodiment, two pathogens are obtained—one of human origin and one of canine origin. Enterotoxigenic $E.\ coli$ O8:H9 (ETEC) of human origin was provided by the Centre Hospitalier Universitaire Vaudoise (CHUV), Lausanne, Switzerland. $E.\ coli$ LTH 1577 O149:K88 (CEC; pathogenic isolate of canine origin) was provided by Prof. W. P. Hammes, University of Hohenheim, Germany. Permanent stock cultures were maintained by storing at −80° C. in cryoprotective medium (containing 30% glycerol and 50% Brain Heart Infusion; BHI). All pathogens were cultivated in BHI at 37° C. under aerobic conditions.

The method further includes exposing the probiotic to a gastric juice. Candidate probiotics were screened for survival in conditions designed to mimic the canine stomach. Gastric juice was simulated with 0.3% porcine pepsin (P-7000) in 0.5% NaCl, with the pH adjusted to two decimals less than desired in the test using HCl. Two pH regimens were tested: incubation for 10 minutes at pH 2.6 or incubation for 60 minutes at pH 3.4. All incubations were performed aerobically at 37° C.

To start the test, 1.5 mL 0.5% NaCl and 1 mL of bacterial suspension (after overnight culture in MRS, 2 ml aliquots of each strain were washed three times and resuspended in 2 ml 0.9% NaCl) were added to 5 mL gastric juice, the pH recorded and cell counts performed ($t_0$). pH values and cell counts were repeated at the end of the test ($t_{10}$ or $t_{60}$).

The method further includes providing a model of a pet small intestine. A model of the canine small intestine was constructed following adaptation of previous data. The model was composed of a combination of tauroconjugated bile salts (74% taurocholic acid, 8.4% taurochenodeoxycholic acid, 17% taurodeoxycholic acid, 0.15% cholic acid), enzymes, dog food, and $CaCO_3$. A 5× stock solution of bile salts was prepared in electrolyte solution (NaCl 5 g/L, KCl 0.6 g/L, and $CaCl_2$ 0.25 g/L) and stored at −80° C., containing taurodeoxycholate (T-0875; 7 g/L), taurocholate (T-4009; 30.4 g/L), cholate (27028; 60 mg/L) and taurochenodeoxycholate (T-6260; 3.4 g/L). 10× stock solutions of mucin (M-2378; 19 g/L) and of pancreatin (P-1500; 24.2 g/L; according to) were similarly prepared.

In an embodiment, a 5× stock solution of standard dry dog food (100 g/L water) was prepared, and contained less than 1 mM of sugars (0.8 mM glucose and 0.2 mM fructose) and about 5% starch. A model mastermix was prepared in a sterile 250 mL beaker by mixing stock solutions; for each test 1 mL of mucin, 1 mL of pancreatin, 2 mL of bile salts and 2 mL of pet food were combined and then made up to 9 mL with electrolyte solution. The pH of mastermix was measured and adjusted to 6.7±0.2.

Each candidate probiotic strain was co-incubated with a pathogen in the mastermix. As a control, the pathogen was incubated without addition of a probiotic. This allowed determination of inhibition of pathogen growth and resistance of probiotic to these conditions, and the measurement of the production of anti-pathogenic metabolites (organic acids and hydrogen peroxide). The candidate probiotics were prepared by anaerobically incubating overnight in plastic tubes containing 10 mL MRS, then washing three times in electrolyte solution, and finally centrifuging to a pellet. The pathogens were prepared by aerobic incubation in BHI, at 37° C. for 4-5 h, and then adjusted to $10^4$ to $4 \times 10^4$ cells/mL in tryptone saline (TS; NaCl 8.5 g and tryptone 1.0 g in 1 L water, adjusted to pH7).

For each test, 9 mL of the mastermix and 1 mL of $CaCO_3$ buffer ($CaCO_3$ 20 g/L suspension) were added to the probiotic pellet (final count 8.5±0.4 log colony-forming-unit (CFU)/mL) and 50-200 μL of pathogen solution (final count 3.0±0.1 log CFU/mL) in a plastic tube. The plastic tubes were closed and incubated with shaking (100 rpm) for 6-7 h at 37° C. Samples were taken directly after addition of the pathogen to the model and at the end of the incubation period for enumeration of probiotic and pathogen counts (both by plating), and analysis of organic acid content, hydrogen peroxide content, and pH. 100 μL and 500 μL aliquots were taken for direct plating on MC agar (for enumeration of pathogen counts). Ten-fold dilutions of 100 μL aliquots were conducted 6 times in TS, and plated on MRS agar plates (supplemented with polymixin) for enumeration of probiotic counts. The plates were incubated at 37° C. overnight (MC aerobically, MRS anaerobically).

Organic acids were analyzed by routine HPLC (Hewlett Packard Series 1100; Aminex HPX-87H 300×7.8 mm (Bio-Rad) column; 5 mM $H_2SO_4$ as eluent; flow rate 0.6 mL/min). Peroxide was quantified enzymatically with horseradish peroxidase and 2,2'-azino-bis(3-ethylbenzothiazoline-6-sulfonic acid) diammonium salt (ABTS) as chromogenic substrate. The samples were diluted in pH 4 buffer (0.1 M citric acid/0.2 M disodiumhydgrogenphosphate) to about 1-10 μM $H_2O_2$. 500 μL of the dilutions were mixed with 500 μL freshly prepared assay buffer (0.4 mM ABTS, 1 U/ml peroxidase P8250 in pH 4 buffer) and the OD was measured at 420 nm.

The relevance of lactic acid as an anti-pathogenic strategy was investigated using a parallel study design. In a mastermix culture containing ETEC and probiotic strain 39b, the pH was measured every 30 minutes for 8 h. These pH changes were mimicked, by the addition of lactic acid, in the parallel culture (which contained ETEC only). Cell counts of ETEC were performed in both at 0 h, 2 h, 4 h, 6 h, 8 h and 22 h.

The relevance of hydrogen peroxide as an anti-pathogenic metabolite was investigated by incubating approximately 3 log CFU/mL ETEC with different concentrations of either hydrogen peroxide, or the supernatant from probiotic strain 56a, at 37° C., and measuring cell counts at 0 h, 4 h and 24 h. Supernatant from strain 56a was obtained by washing an overnight culture twice, then resuspending (about 9 log CFU/mL) in the same volume of NB (Nutrient Broth), and incubating for 6 h at 37° C. (at a constant pH of 7.0); this culture was then centrifuged and the supernatant filtersterilized (0.2 µm).

Results

Seventy-five strains of lactobacilli were initially identified from a variety of fecal samples (obtained from 17 healthy dogs), and of these, 16 strains (all typed as *L. acidophilus, L. reuteri, L. salivarius,* or *L. johnsonii*) showed significant anti-pathogenic activity in the model and resistance to gastric conditions. Six of these strains provide effective probiotics for dogs. Survival of candidate probiotic strains was high following incubation in conditions designed to mimic the canine stomach (Table E). All strains were stable when incubated for 10 minutes at pH 2.6, losing less than one log CFU/mL. All strains were stable when incubated for 60 minutes at pH 3.4, losing less than one log CFU/mL.

Survival of candidate probiotic strains was high following incubation in conditions designed to mimic the canine small intestine (Table F). *L. acidophilus, L. reuteri,* and *L. salivarius* strains were stable when incubated in the mastermix in the presence of enterotoxigenic *E. coli* (ETEC), losing less than one log CFU/mL. *L. johnsonii* strains were less stable, losing more than one log CFU/mL, due to the high level of peroxide production by this species. The candidate probiotics exhibited high anti-pathogenic activity indicated by complete inactivation of *E. coli* ETEC in the mastermix. *L. johnsonii* strains inhibited the growth of ETEC to the greatest extent, followed by *L. acidophilus,* then *L. salivarius* strain (Table G). *L. johnsonii* strain 56a was also tested against the pathogenic *E. coli* strain of canine origin (CEC), and following a 6 h incubation in the mastermix, the pathogen was completely inactivated (the change in pathogen growth was −2.8 log CFU/mL (n=1)). Strain 56a similarly inhibited two other pathogens of human origin: *Salmonella typhimurium* and *Shigella dysenteriae* (data not shown). *L. acidophilus* strain 39b was also tested against the canine *E. coli* isolate (CEC), and following a 6 h incubation in the mastermix (although containing 2 mL 5 g/L dextrose rather than pet food), the pathogen was completely inactivated (the change in pathogen growth was −2.2 log CFU/mL (n=1)). Strain 39b similarly inhibited two other pathogens of human origin: *Salmonella typhimurium* and *Shigella dysenteriae* (data not shown).

The different *lactobacillus* species studied utilized different anti-pathogenic strategies, and were found to produce different metabolites in the mastermix. When incubated with ETEC, *L. acidophilus* strains greatly reduced the pH of the mastermix (to pH 4.5) and produced high amounts of lactic acid (in the range of 70-90 mM). However, hydrogen peroxide production by this species was relatively low (Table G). In contrast, *L. johnsonii* strains had a less marked effect on pH (pH 5.2), and produced less lactic acid (in the range of 10-17 mM), but this species produced high amounts of hydrogen peroxide (in the range of 3-4 mM) (Table G). The *L. salivarius* strain studied combined these principles, but showed less anti-pathogen activity than the other species, lowering pH to 4.8 and producing some lactic acid and relatively low amounts of hydrogen peroxide (Table G).

The results indicated that these strategies were the main cause for pathogen inhibition was demonstrated in separate experiments. The growth of ETEC was mainly influenced by pH, with partial inhibition at around pH 5, and complete inactivation when the pH was reduced to pH 4.7 or below (data not shown).

Lactic acid production by *L. acidophilus* was confirmed as an anti-pathogen strategy. The effect of probiotic strain 39b and the artificial acidification by lactic acid (mimicking the pH curve demonstrated by the probiotic) had similar effects on the growth of ETEC in the mastermix (data not shown).

Hydrogen peroxide production by *L. johnsonii* was confirmed as an anti-pathogen strategy. The effect of co-culturing the supernatant of strain 56a with ETEC was similar to that observed with equivalent concentrations of hydrogen peroxide itself, and these effects were dose-responsive (data not shown). Separate studies showed that moderate concentrations of hydrogen peroxide (>0.35 mM) transiently inhibited the growth of ETEC, but the addition of high levels of hydrogen peroxide (>0.9 mM) for 4 h was bactericidal (data not shown). Production of hydrogen peroxide and lactic acid was independent from the presence of a pathogen.

The six candidate probiotics isolated from the feces of healthy dogs were resistant to canine gastrointestinal conditions and demonstrated efficacy against relevant pathogens. Originating naturally from healthy dogs, these canine-specific strains are well adapted to the canine intestinal system and therefore potentially more efficacious when administered as a probiotic than LAB obtained from other species. It is suggested that probiotic adhesion to the gut epithelia or the mucus of the host, probably via specific receptors, increases gut barrier functions and establishes a transitory colonization of the probiotic, thereby competitively excluding pathogens.

Canine lactobacilli are adapted to the canine gut and also to the carbohydrates prevalent in this environment. Efficient substrate utilization is an important factor for adaptation to an ecological niche resulting in competitiveness and survival. *L. acidophilus* and *L. johnsonii* were the most efficacious species, providing the only strains with the ability to ferment starch, the main carbon source in pet food. As starch utilization is not characteristic for *L. acidophilus/L. johnsonii*—this ability shows the high degree of adaptation to the ecological niche. *L. reuteri* and *L. salivarius* strains were less efficacious against pathogens in the model, and being unable to utilize starch, these LAB were probably using the sugars resulting from enzymatic starch breakdown.

The Lactobacilli identified on the present method produced many anti-microbial substances, mainly organic acids, especially lactic acid, but also hydrogen peroxide, bacteriocins and reuterin. Lactic acid was proven to be the primary effector of the low pH exhibited by *L. acidophilus*. Acidification is a very effective anti-pathogenic strategy; below pH 4.7, ETEC was not only inhibited, but completely inactivated (killed). The probiotic strains were stable and physiologically active at these low pH values, which is important in vivo, since studies in fistulated dogs show that duodenal pH decreases to around 3.5-5.9 during the first few hours following a meal. This strongly suggests that these probiotics will be equally effective in vivo.

Other anti-pathogenic strategies were evident in the LAB studied here. Hydrogen peroxide is a well-recognized anti-microbial metabolite which results in the production of reactive oxygen species, inhibiting a wide variety of bacteria, and killing *E. coli* at 0.5 mM. Hydrogen peroxide was a major strategy utilized by the *L. johnsonii* strains, which produced less lactic acid and so had only a moderate pH lowering effect. The *L. salivarius* strain appeared to use a combination of lactic acid and hydrogen peroxide production, and possibly additional, unidentified anti-pathogen strategies.

The pathogenic species utilized in this model are recognized canine enteropathogens. Canine varieties of pathogenic *E. coli*, ETEC and EPEC, have been implicated in enteric infectious diseases in dogs and *E. coli* is frequently implicated in small intestinal bacterial overgrowth. In humans and farm animals, ETEC has been shown to colonize the proximal part of the small intestine, the critical site for host-parasite interactions. Although not fully tested in the current study, probiotics are also likely to be effective against a range of other canine enteric pathogens, for example, *salmonella*, *campylobacter* and *clostridium*, due to the broad spectrum of the antimicrobial principles. In addition, there are a range of non-infective diarrheal conditions that might be alleviated by simply balancing the gut microflora, including those resulting from weaning, dietary changes and stress. These beneficial effects are in addition to the known immuno-modulatory role of probiotics that could increase gastrointestinal defenses.

The present in vitro method for assessing the efficacy candidate probiotics in a simulated canine gastrointestinal tract strongly suggests that the probiotic properties observed in vitro will be exerted in vivo. The present method provides an excellent preliminary approach for screening probiotics for likely efficacy in a pet. Any limitations in using an in vitro system are amply offset by the reduction in the requirement for in vivo studies, thereon advantageously eliminating any ethical limitations of challenge tests.

TABLE E

Resistance of candidate probiotics to conditions mimicking the canine stomach. Data show the change in probiotic growth (Mean ± SD delta log CFU/mL) following aerobic incubation in simulated gastric juice at 37° C., in the absence of pathogens, at the two pH regimens indicated.

| | | 10 min pH 2.6 | | 60 min pH 3.4 | |
|---|---|---|---|---|---|
| Species | Strain | mean (n = 4) | SD | mean (n = 4) | SD |
| L. acidophilus | 38 (=NCC2766) | −0.5 | 0.1 | −0.2 | 0.2 |
| L. acidophilus | 45b (=NCC2775) | −0.1 | 0.0 | −0.1 | 0.0 |
| L. acidophilus | 39b (NCC = 2628) | −0.1 | 0.2 | 0.0 | 0.1 |
| L salivarius | 14a | −0.3 | 0.2 | −0.1 | 0.2 |
| L. johnsonii | 56a (=NCC2777) | −0.3 | 0.2 | −0.1 | 0.3 |
| L. johnsonii | 41b (=NCC2767) | −0.3 | 0.1 | −0.8 | 0.1 |

TABLE F

Resistance of candidate probiotics to conditions mimicking the canine small intestine. Data show the change in probiotic growth (Mean ± SD delta log CFU/mL) following 6-7 h incubation in simulated small intestinal juice at 37° C., in the presence of ETEC.

| Species | Strain | mean (n = 4) | SD |
|---|---|---|---|
| L. acidophilus | 38 (=NCC2766) | −0.3 | 0.1 |
| L. acidophilus | 45b (=NCC2775) | 0.2 | 0.5 |
| L. acidophilus | 39b (=NCC2628) | −0.1 | 0.3 |
| L salivarius | 14a | −0.7 | 0.4 |
| L. johnsonii | 56a (=NCC2777) | −2.6 | 0.6 |
| L. johnsonii | 41b (=NCC2767) | −2.0 | 1.0 |

TABLE G

Anti-pathogenic efficacy and mechanisms of candidate probiotics. Data show the change in pathogen growth (Mean ± SD delta log CFU/mL), the post-incubation pH, lactic acid and hydrogen peroxide concentrations, following 6-7 h incubation of probiotic in simulated small intestinal juice at 37° C., in the presence of ETEC.

| | | | ETEC delta log CFU/mL | | Final pH | | Lactic acid $(mM)^2$ | | Hydrogen peroxide (mM) | |
|---|---|---|---|---|---|---|---|---|---|---|
| Species | Strain | $n^1$ | mean | SD | mean | SD | mean | SD | mean | SD |
| L. acidophilus | 38 (=NCC2766) | 3 | −1.9 | 0.5 | 4.5 | 0.0 | 87.0 | 6.0 | 0.7 | 0.2 |
| L. acidophilus | 45b (=NCC2775) | 6 | −1.9 | 0.9 | 4.5 | 0.0 | 82.0 | 18.0 | 0.1 | 0.0 |
| L. acidophilus | 39b (=NCC2628) | 2 | −1.1 | 0.4 | 4.5 | 0.0 | 72.0 | 28.0 | 0.5 | 0.0 |
| L. salivarius | 14a | 2 | −0.9 | 0.2 | 4.8 | 0.3 | 52.0 | 4.0 | 0.2 | 0.0 |
| L. johnsonii | 56a (=NCC2777) | 7 | −2.8 | 0.3 | 5.4 | 0.1 | 10.0 | 2.0 | 4.1 | 0.6 |
| L. johnsonii | 41b (=NCC2767) | 3 | −2.0 | 1.0 | 5.0 | 0.1 | 17.0 | 3.0 | 3.2 | 0.5 |
| Control (no probiotic) | — | 6 | 5.6 | 0.5 | 5.8 | 0.2 | 2.0 | 2.0 | 0 | 0 |

[1]Except for hydrogen perocide measurements, where n = 4 for all strains.
[2]Minor amounts of other organic acids were recorded (acetic, succinic, citric and pyruvic acids) - date not shown.

The present invention is not to be limited in scope by the specific embodiments described herein. The examples are preceded by a brief description of the figures.

Figures

FIG. 1: Lymphocyte proliferation of canine peripheral blood mononuclear cells (PMBC) upon stimulation with mitogens or phorbol esters. PMBC from adult dogs fed during 4 weeks with (Black bars) or without (White bars) *L. acidophilus* NCC2628 were stimulated with different mitogens at doses (μg/ml) indicated in the graphic. Mitogens are PHA (Phytohemaglutin), ConA (Concanavalin A), PWM (Pokeweed mitogen) and phorbol ester are PMA/iono (Phorbol myristate acetate and ionomycin). *=P<0.05, Student's t test.

Figure 2:
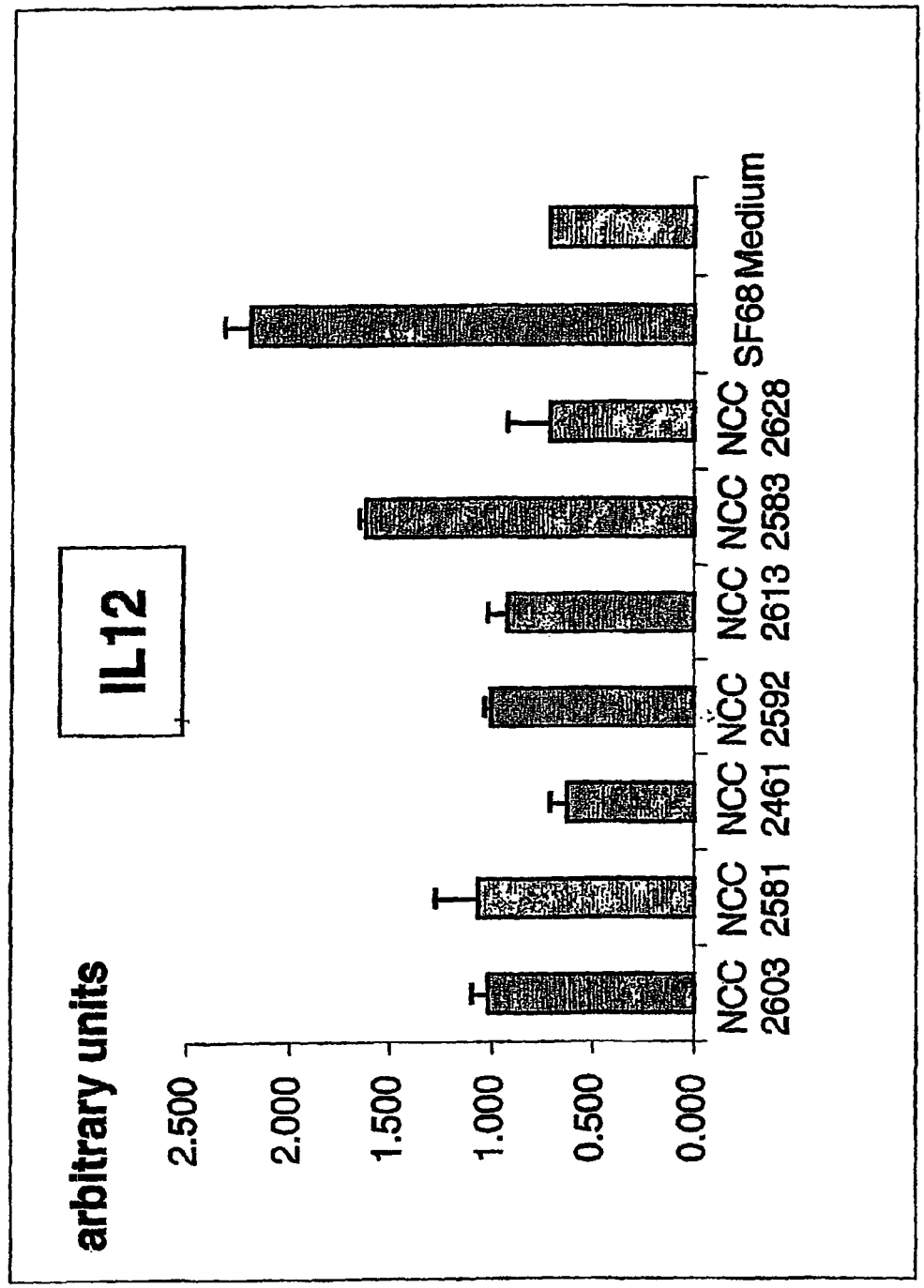
FIGS. 2A-2D are graphs showing the results in arbitrary units of cytokines produced by canine leucocytes upon stimulation with various strains of probiotics.
Figure 2:
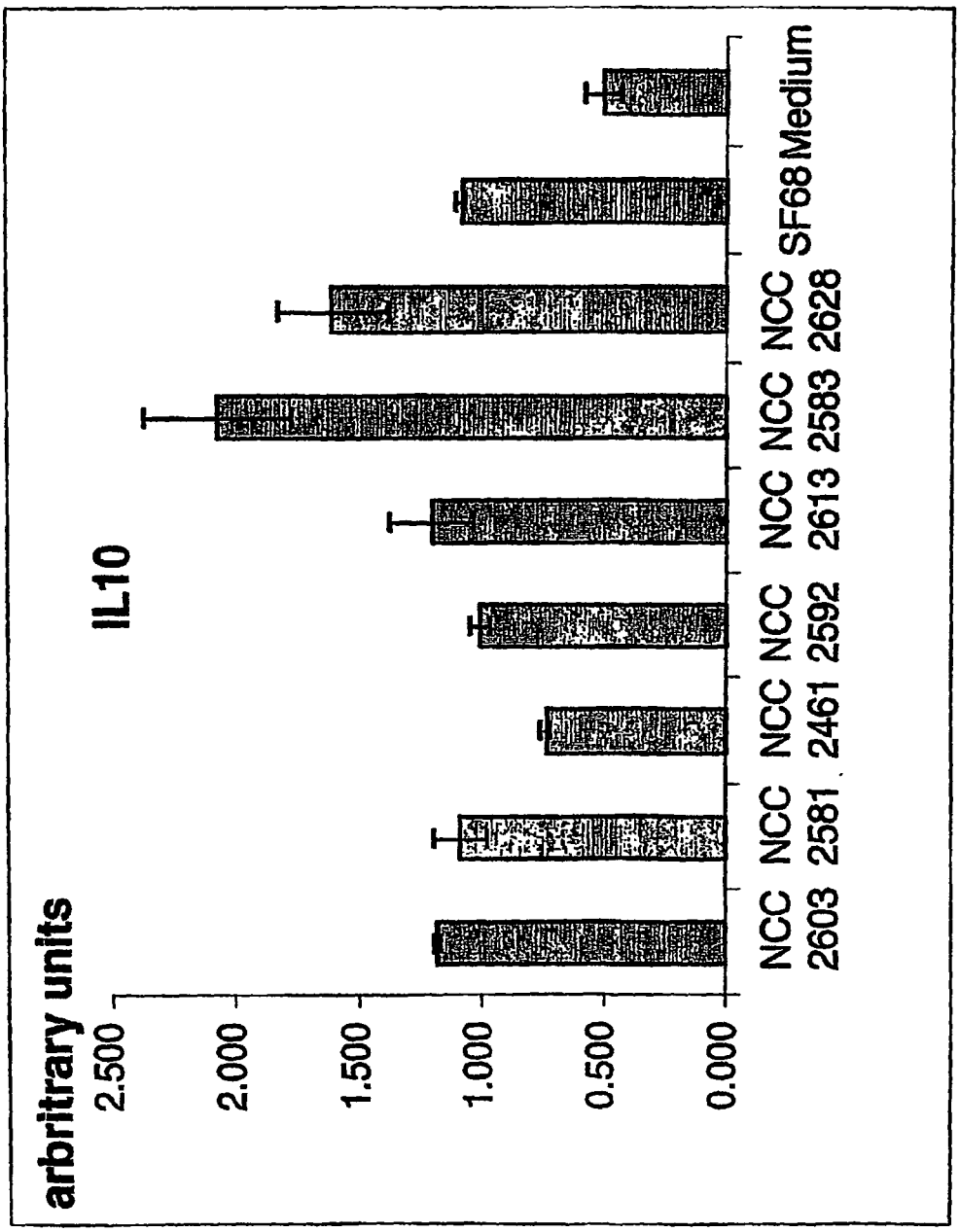
Figure 2:
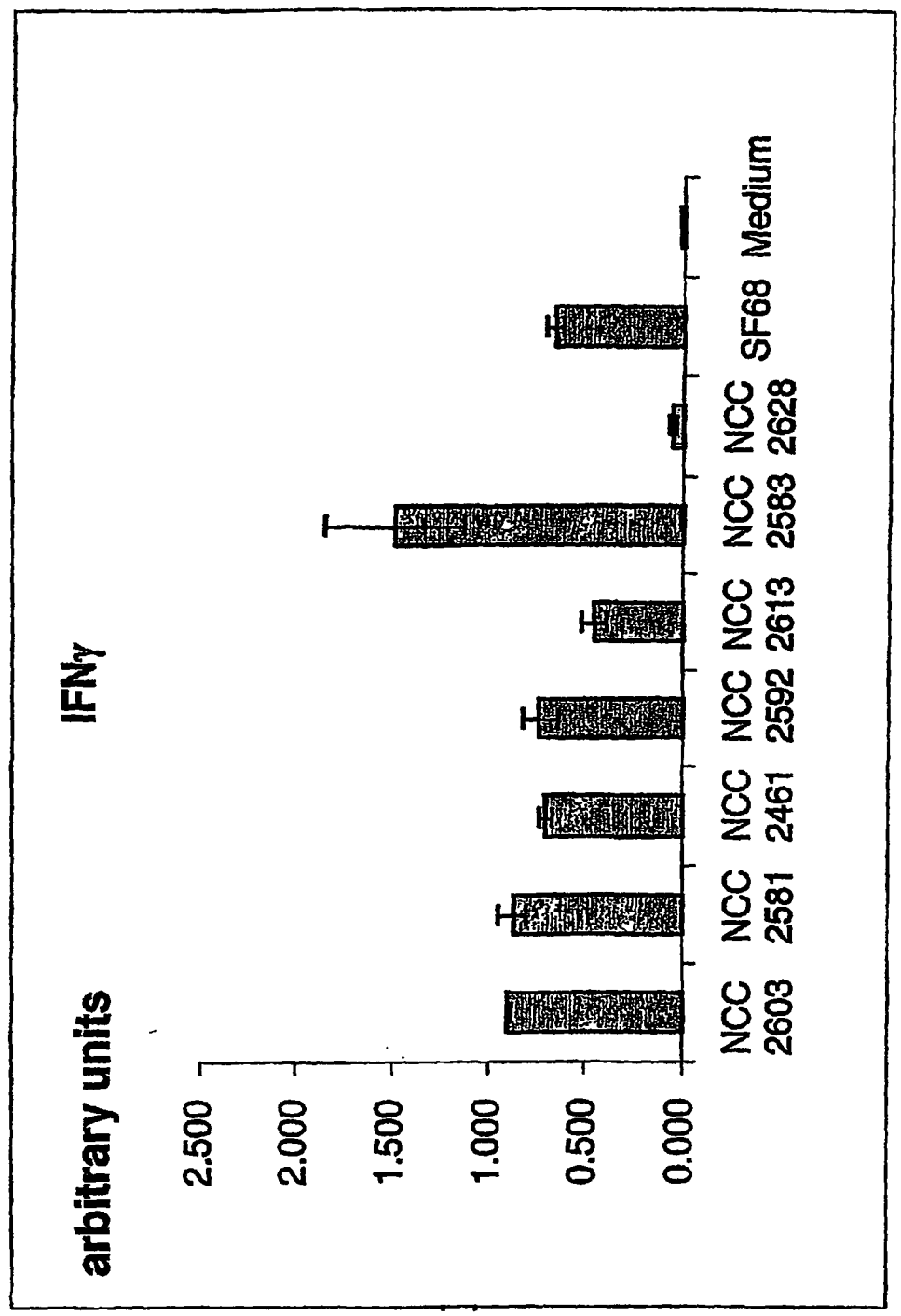

FIG. 2: Cytokines produced by canine leucocytes stimulated with different strains of probiotics. Leucocytes from normal adult dogs were stimulated with different pet-isolated *lactobacillus* strains for 18 h. Control cultures contained medium alone (negative control) or a human *lactobacillus* isolate ST11 (positive control). Identification of cytokines was done by RT-PCR. Their quantification was performed by scanning the ethidium bromide-strained agarosgels and determining the relative pixel of each band using the NIH Image software. The results are expressed as the means of two independent experiments in arbitrary units. (A) IL-12, (B) IL-10, (C) IFNγ, (D) TGFβ.

EXAMPLES

Example 1

Strains and Culture Conditions

Numerous strains (from the Nestle culture collection=NCC) were screened for their potential probiotic use for cats and dogs. In particular, growth potentials, resistance to freeze-drying with subsequent storage, tolerance to gastric acidity and different concentrations of bile salts found in the gastrointestinal tract of cats and dogs, were assessed for those 20 lactobacilli and 18 bifidobacteria isolated from cat and dog faeces presented in Table 1.

TABLE 1

Codes and characteristics of bacteria selected for the assays

*Lactobacilli*:

| NCC-Code | CNCM-Code | Code | Animal species origin | Type of diet intake | NH3 from arginine | Lactic acid | Identified with API50CH |
|---|---|---|---|---|---|---|---|
| 2578 | — | LB1-1 | Cat | Mixed | − | L | *L. animalis/ruminis* |
| 2581 | I-2448 | LB1-2 | Cat | Mixed | + | D/L | *L. reuteri* |
| 2583 | I-2449 | LK1-1 | Cat | Mixed | − | D/L | *L. rhamnosus* |
| 2586 | — | LK1-2 | Cat | Mixed | + | D/L | *L. reuteri* |
| 2590 | — | LH2-1 | Cat | Dry | − | D/L | *L. acidophilus* |
| 2592 | I-2450 | LR1-1 | Cat | Mixed | + | D/L | *L. reuteri* |
| 2594 | — | LS1-1 | Cat | Mixed | − | L | *L. animalis/ruminis* |
| 2597 | — | LA2-5 | Dog | Wet | − | L | *L. animalis* |
| 2600 | — | LC2-5 | Dog | Wet | − | D/L | *L. fermentum/reuteri* |
| 2603 | I 2451 | LE2-5 | Dog | Wet | − | L | *L. reuteri* |
| 2606 | — | LE2-6 | Dog | Dry | + | D/L | *L. reuteri* |
| 2609 | — | LH2-6 | Dog | Dry | + | D/L | *L. reuteri* |
| 2613 | I-2452 | LH2-7 | Dog | Dry | + | D/L | *L. reuteri* |
| 2616 | — | L1-1-1 | Dog | Mixed | + | D/L | *L. reuteri/fermentum* |
| 2619 | — | L1-1-2 | Dog | Mixed | − | D/L | *L. acidophilus* |
| 2621 | — | L3-1-2 | Dog | Mixed | − | L | *L. animalis/ruminis* |
| 2625 | — | L7-1-3 | Dog | Mixed | − | L | *L. animalis/ruminis* |
| 2628 | I-2453 | LA1-5 | Dog | Mixed | − | D/L | *L. acidophilus* |
| 2632 | — | LA1-6 | Dog | Mixed | + | D/L | *L. reuteri/fermentum* |
| 2636 | — | LB1-5 | Dog | Mixed | − | L | *L. animali/ruminis* |

*Bifidobacteria*:

| NCC Code | Code | Animal species origin | Type of diet intake | Species |
|---|---|---|---|---|
| 2623 | CO2-5 | Cat | Dry | *Bifidobacterium* |
| 2627 | CG2-5 | Cat | Dry | *Bif. adolescentis* |
| 2630 | CH2-5 | Cat | Dry | *Bif. adolescentis* |
| 2533 | CE3-1 | Cat | Dry | *Bif. adolescentis* |
| 2635 | CC1-5 | Cat | Mixed | *Bif. longum/suis* |
| 2637 | CE4-1 | Cat | Dry | *Bif. adolescentis* |
| 2640 | CB3-5 | Cat | Dry | *Bif. adolescentis* |
| 2643 | CJ2-6 | Cat | Dry | *Bif. adolescentis* |
| 2647 | D5-3-5 | Dog | Wet | *Bif. adolescentis* |
| 2651 | D8-3-6 | Dog | Dry | *Bif. animalis/lactis* |
| 2654 | D9-3-7 | Dog | Dry | *Bif. animalis/lactis* |
| 2657 | D6-3-6 | Dog | Dry | *Bifidobacterium* |
| 2660 | D7-3-5 | Dog | Dry | *Biftobacterium* |
| 2663 | DB3-1 | Dog | Dry | *Bifidobacterium* |
| 2667 | DC3-1 | Dog | Dry | *Bifidobacterium* |
| 2671 | DA1-3 | Dog | Mixed | *Bif. animalis/lactis* |
| 2574 | DA3-1 | Dog | Dry | *Biftobacterium* |
| 2677 | DD3-1 | Dog | Dry | *Bif. adolescentis* |

All 20 lactobacilli and 18 bifidobacteria were isolated from cats and dogs kept on different diets, as shown in Table 1. Initial identification was determined by morphological and physiological characteristics. API-50CH and Rapid-ID32A systems (BioMerieux) were used for lactobacilli and bifidobacteria, respectively. Pure strains were frozen and deposited at −80° C. in the Nestec-Culture-Collection (NCC).

All bacteria were cultured in broth-medium for the assays. A sample from each reactivated strain was stored at −80° C. in 1 ml-cryoprotective media (40% glycerol+60% LL). The cultures were maintained by subculturing on a weekly base a 1% inocula in 10 ml-growth medium and anaerobic incubation at 37° C.

Lactobacilli were grown in MRS for 18 hours. Bifidobacteria were grown either in MRS+0.05% (w/v) L-cysteine hydrochloride (MRS-C) for 32 hours or in BHI+0.05% L-cysteine hydrochloride (BM-C) for 48 hours starting with a 5% inoculum.

All cultures were stored at +4° C. between the different transfers. Anaerobiosis was generally obtained using a hydrogen-carbon dioxide anaerobic system (GasPak, Becton Dickinson, USA). Bifidobacteria were always kept in these jars during their storage period.

Example 2

Selection of Bacterial Strains

This in-vitro screening was based on production characteristics for an industrial application of viable cells, their ability to survive inhibiting or detrimental gastrointestinal conditions and their genomic diversity. Strain diversity or genomic similarity of those non-characterized strains was taken into account, using RAPD and ribotyping.

Materials and Methods

Bacterial Growth

The strains that are able to produce rapidly high number of cells have to be identified. Their bacterial growth cycle can be characterized by a short lag phase, a short generation time, high maximal counts and a long stationary phase. Therefore, strains were compared by considering three variables: the length of their lag phase, their generation time (in hours) and their maximal counts, which corresponded to the most important characteristics.

For Lactobacilli:

200 ml MRS broth preincubated at 37° C. was inoculated with 1% of a fresh subculture. One ml samples were collected at every hour post inoculation for eight hours. A final sample was taken after 24 h. One ml of each sample was 10-fold serially diluted in TS for enumeration. Cultures were grown in MRS agar (pour-plating technique), anaerobically, at 37° C., for 48 hours. All plates with colony-numbers between 30 and 350 were recorded as colony forming units (cfu) per ml of culture and were therefore taken into consideration for enumerations.

For Bifidobacteria in (MRS-C):

In preliminary assays, all strains were enumerated after 24 h growth in MRS-C and TPYG broth. Results were expressed in cfu/ml. The growth curves were established by determining the cell numbers when grown in MRS-C after 0, 4, 12, 24, 32 and 48 h, according to the protocol described for lactobacilli. In order to determine the influence of the subculture medium and of optimization of degassing the growth medium, this assay was realized:

from a subculture, in BHI-C stored 48 h at 4° C., and inoculated in MRS-C from a subculture, in BHI-C stored 48 h at 4° C., and inoculated in MRS-C well degassed (removal of oxygen had been optimized by autoclaving the medium twice and storing it directly in anaerobic jars)

from a fresh subculture, in MRS, and inoculated in MRS-C well degassed and stored under anaerobic conditions before the experiment

TABLE 2

Test media for bacterial growth

| Substrate | Composition | | pH | References |
|---|---|---|---|---|
| For *lactobacilli* | | | | |
| MRS | MRS without sugar (Difco) | 35 g·l$^{-1}$ | 6.5 | De Man and al. (1960) |
| | Glucose | 20 g·l$^{-1}$ | | |
| | Distilled water | 1,000 ml | | |
| For *bifidobacteria* | | | | |
| MRS-C | MRS without sugar (Difco) | 35 g·l$^{-1}$ | 6.0 | Pacher and Kneifel (1996) |
| | Glucose | 20 g·l$^{-1}$ | | |
| | L-cysteine HCl (Fluka) | 0.5 g·l$^{-1}$ | | |
| | Distilled water | 1,000 ml | | |
| TPYG (Trypticase Peptone Yeast Extract) | Trypticase (BBL) | 50 g·l$^{-1}$ | 7.0 | |
| | Peptone (Difco) | 5 g·l$^{-1}$ | | |
| | Yeast extract (Difco) | 20 g·l$^{-1}$ | | |
| | Glucose (Merck) | 4 g·l$^{-1}$ | | |
| | L-cysteine HCl (Fluka) | 1 g·l$^{-1}$ | | |
| | Distilled water | 1,000 ml | | |

Solid media were obtained by the addition of Difco Bacto agar (15 g.l$^{-1}$). Media were autoclaved at 121° C. for 15 min. Liquid media for bifidobacteria were either stored under anaerobic conditions or degassed before utilization.

Resistance to Gastric pH and Bile

When ingested, the micro-organisms have to survive stomach and duodenum conditions to be able to exert a beneficial activity in the gastrointestinal tract of the animal. Gastric pH and biliary salts are the main components responsible for regulation of bacterial flora. Therefore, the degree of resistance of the strains to acidity and bile has to be assayed.

The physiology of the digestive tract of cats and dogs differ from humans. The average pH were pH 3.4 and 4.2 respectively in dogs and cats. A reconstituted pet bile was recommended for the assays (Table 4). The bile concentration in the small intestine varies in a range of 0.5 to 2% when food is digested.

According to extreme pH values found in cats and dogs, viable counts after 10 minutes at pH 2.6 and after two hours at either pH 3.4 (strains isolated from dogs) or pH 4.2 (strains isolated from cats) should not be below 1.0E+06 cfu/ml.

Resistance to Gastric pH

All lactobacilli were inoculated at 1% in MRS broth and grown anaerobically at 37° C. overnight. Bifidobacteria, inoculated at 5% in BM-C, were grown 48 hours at 37° C. under anaerobic conditions. The cultures were dispensed in two ml reaction tubes (Eppendorf) and centrifuged at 3,500× g/10 min/20° C. Cells were washed three times with Ringer-solution. The resistance to stomach acidic conditions was assayed in-vitro in three simulated gastric juices with pH levels of 2.6, 3.4 and 4.2 adjusted with HCl (Merck). Disposable filterware (Nalgene) was used for all filter-sterilizations. The survival of each bacterial suspension was studied by adding one ml into a series of five ml of simulated gastric juice (different pHs) supplemented with 1.5 ml of a 0.5% NaCl solution.

The samples were incubated at 37° C. and the viable organisms enumerated at 0, 1, 5, 10 minutes with the pH 2.6 gastric juice 0, 1, 30, 60, 120, 180 minutes when the gastric juice had a pH of either 3.4 (for strains isolated from dogs) or 4.2 (for strains isolated from cats)

Samples were diluted in phosphate buffer (pH 7.0), plated onto MRS-C agar and enumerated.

TABLE 3

Simulated gastric juice

| Substrate name | Composition | PH |
|---|---|---|
| Gastric juice | 0.3% w/v porcine pepsin (Sigma) 0.5% w/v NaCl HCl (Merck): to adjust pH | 2.1, 3.4 or 4.2 |

Resistance to Bile Salts

The evolution of the viable counts of lactobacilli grown for 18 hours in presence of various concentrations of reconstituted pet bile was determined.

Two viable counts were considered significantly different when the deviation of their $\log_{10}$ was above 0.25. Each strain was characterized by two variables:

the maximal bile salt concentration tested where no significative difference with the control was found the rate of the decrease in viability when bile concentration in the growth medium increases The strains characterized by a loss superior to a $\log_{10}$ of their viable counts when bile concentration raises in 1% steps were considered sensitive to bile. A reduction superior to one $\log_{10}$ between cells grown in presence of 0 and 2% bile, and to one $\log_{10}$ per additional percent of bile (above 2%) was considered acceptable. Furthermore, only strains producing more than 1.0E+06 cfu/ml when grown in presence of up to 2% bile salts should be selected, in order to produce an effect in the gastrointestinal tract.

Reconstituted pet bile from cats or dogs was prepared as indicated in Table 4, and filter sterilized prior to use. In a first assay, lactobacilli were grown anaerobically for 24 hours in MRS broth at 37° C. and transferred into fresh MRS broth plus 0, 0.1, 0.3, 0.5, 1, 2, 4% sterile reconstituted pet bile for additional 18 hours. Samples were 10-fold serially diluted in TS for enumeration. Dilutions 1.0E-03 and 1.0E-05 were plated onto MRS agar, using a WASP (Whitley Automatic Spiral Plater; Don Whitley Scientific Limited, England). When dried, the plates were inverted and incubated 48 hours at 37° C. in anaerobic jars.

Floch and al. (1972) defined an inhibition as significant when at least 2 logs in the test compared with the control tube growth were reduced. Based on this, all the lactobacilli sensitive to bile concentrations in the first assay and two lactobacilli resistant to 4% bile were tested similarly in presence of 0, 1, 1.5, 2, 2.5, 3, 4% bile. The second test aimed for a repeatability and established if the number of viable bacteria decreased dramatically with increasing bile concentration.

On the other hand, it pointed out that these strains are bile-resistant during this 18 h-period. Growth curves were established in presence of bile salts to determine if the lag phase and the growth rate were affected or not. Assays were undertaken with lactobacilli grown in MRS broth supplemented with 1% reconstituted pet bile, according to the protocol described for earlier growth measurement.

The bifidobacteria were subcultured and grown 32 hours/37° C./anaerobically, using MRS-C broth with 0, 1, 2, 3 and 4% reconstituted pet bile. The same enumeration method at dilutions 1.0E-03, 1.0E-04 and 1.0E-05 was applied as for lactobacilli.

TABLE 4

Reconstituted pet bile

| Compounds | µmol/ml | mg/ml | % total |
|---|---|---|---|
| Taurodeoxycholate (Sigma) | 14.00 | 7.00 | 18.0 |
| Taurocholate (Sigma) | 59.00 | 30.40 | 74.0 |
| Cholate (Fluka) | 0.14 | 0.06 | 0.2 |
| Taurachenodeoxycholate (Sigma) | 6.90 | 3.45 | 8.0 |

Survival to Freeze-Drying and Subsequent Storage of the *Lactobacillus* Strains

The evolution of survival was evaluated. Viable counts inferior to 10E+05 CFU/ml were considered as being too low.

For each strain, 200 ml MRS broth was inoculated at 3% with a fresh subculture. The cultures were grown for 16 hours at 37° C. Unaerated conditions (closed containers) were assumed to be essentially anaerobic. Viable cells were enumerated, using the pour-plating method described earlier.

The cultures were harvested by centrifugation at 3,500× g/+7° C./20 minutes (RC3C Sorvall Instrument centrifuge) and resuspended in 10 ml of two different cryoprotective media. Each strain was resuspended in two different cryoprotectants. Concentrated bacterial suspensions were enumerated (pour plating method) and dispensed into vials (0.5 ml per ampoule). The samples were frozen at −196° C. in liquid nitrogen and vacuum dried for 18 hours. After freeze-drying, nitrogen was introduced through the freeze-drier air-admittance valve and all ampoules were sealed. All vials were stored at +4° C. and +20° C. for six months. The number of viable cells per ampoule (for each bacteria and suspension media) was determined monthly.

Results

In the frame of the selection of potential probiotics for cats and dogs, the results of this in-vitro screening of 20 lactobacilli and 18 bifidobacteria, based on their growth potentials, resistance to freeze-drying with subsequent storage, resistance to gastric pH and bile concentrations found in the gastro-intestinal tract of cats and dogs are presented in Table 5.

The 20 lactobacilli were classified with regard to the criteria that they fulfilled in the current study. Four strains showed had good results concerning their growth characteristics, resistance to gastric pH, bile resistance and their survival during storage after to freeze-drying: *L. reuteri* NCC2581 (CNCM I-2448), *L. reuteri* NCC2592 (CNCM I-2450), *L. reuteri* NCC2603 (CNCM I-2451) and *L. reuteri* NCC2613 (CNCM I-2452). The following features were complied:

the generation time was less than one hour when grown in MRS the lag phase was short (less than two hours)

the bacterial counts were high (more than 1.0E+08 CFU/ml) during the stationary phase of the growth cycle and stable at 8 and 24 h post-inoculation the strains were stable through freeze-drying and subsequent six-month storage at 4° C. and 20° C.

the strains were resistant to extreme bile concentration likely to be found in the gastrointestinal tract of cats and dogs (2%)

no significant inhibition in the presence of up to 4% bile in the medium the strains were shown to tolerate pH 2.6 for at least 10 min and could remain at levels higher than 1.0E+08 CFU/ml the strains were resistant to an average gastric pH for at least two hours Therefore, two lactobacilli isolated from cats (*L. reuteri* NCC2581 and *L. reuteri* NCC2592) and two isolated from dogs (*L. reuteri* NCC2603 and *L. reuteri* NCC2613) were selected to be studied for potential probiotic activity. Strains NCC2581, NCC2592, NCC2603 and NCC2613 were identified as *L. reuteri* by API 50CH identification. However, ribotyping revealed that NCC2581 and NCC2592 had very close patterns, as well as NCC2603 and NCC2613, thus indicating a probable close relationship. Strain NCC2581 had very good growth characteristics and NCC2603 had a better resistance to bile than NCC2613.

Results concerning the eight bifidobacteria isolated from cats feces allowed a selection in function of their growth characteristics, their resistance to gastric pH and their bile sensitivity. Strain NCC2623 had none of the desired characteristics, and would therefore not be recommended for further studies. On the other hand, strain NCC2627 fulfilled all the criteria its generation time was less than one hour when grown in MRS-C the lag phase was as short as for lactobacilli counts were high and stable during the stationary phase of the growth cycle the strain was resistant to extreme bile concentration likely to be found in the gastro-intestinal tract of cats and dogs (2%)

no significant inhibition in the presence of up to 4% bile in the medium the strain was shown to tolerate pH 2.6 for at least 10 min and could remain at levels higher than 1.0E+06 CFU/ml the strains were resistant to an average gastric pH for at least two hours The strain NCC2627 was much more resistant than NCC2623 and NCC2635, whereas these three strains had close pattern by ribotyping, therefore indicating a probable close relationship (digestion with two restriction enzymes: EcoRI and EcoRV).

The ten bifidobacteria isolated from dogs showed only two different patterns when characterized by ribotyping. Therefore, bile resistance assays were conducted only with four strains (two from each group): NCC2657; NCC2660, NCC2671 and NCC2677. These four strains were all resistant to maximal concentration of bile that could be found in-vivo (2% bile) and strains NCC2660 and NCC2657 had no decrease in viable counts when subjected to a maximal value of 4% bile. As a consequence, all the bifidobacteria isolated from dogs feces are rather resistant to high concentrations of bile.

Regarding the growth characteristics, these ten bacteria could thereby be divided into two groups:

strains resistant to bile and with good growth characteristics: NCC2657, NCC2651, NCC2663 and NCC2667 strains resistant to bile but with growth characteristics which need to be optimized for industrial production: NCC2660, NCC2671, NCC2677, NCC2647, NCC2654 and NCC2674.

The complete results on resistance to extreme gastric pH found during the digestion of cats and dogs should allow a better determination of the strains to be selected for further studies. Only strain NCC2651 did not fulfill the selection criteria for pH resistance.

TABLE 5

Summary

| NCC Code | Code | Growth criteria | Resistance to gastric juice | Resistance to bile | Stability after freeze-drying |
|---|---|---|---|---|---|
| 2578 | LB1-1 | + | + | − | − |
| 2581 | LB1-2 | + | + | + | + |
| 2583 | LK1-1 | + | + | + | − |
| 2586 | LK1-2 | − | + | − | − |
| 2590 | LH2-1 | + | + | + | − |
| 2592 | LR1-1 | + | + | + | + |
| 2594 | LS1-1 | − | + | − | − |
| 2597 | LA2-5 | − | + | + | + |
| 2600 | LC2-5 | − | − | + | − |
| 2603 | LE2-5 | + | + | + | + |
| 2606 | LF2-6 | − | + | + | − |
| 2609 | LH2-6 | + | + | + | − |
| 2613 | LH2-7 | + | + | + | + |
| 2616 | L1-1-1 | − | + | + | − |
| 2619 | L1-1-2 | − | + | + | − |
| 2621 | L3-1-2 | + | + | − | + |
| 2625 | L7-1-3 | + | +. | − | + |
| 2628 | LA1-5 | + | + | + | − |
| 2632 | LA1-6 | − | + | + | − |
| 2636 | LB1-5 | − | + | + | + |

With regard to current results, one bifibobacterial strain isolated from cats and three bifidobacteria isolated from dogs (respectively NCC2627, NCC2657, NCC2663 and NCC2667) could be selected.

TABLE 6

Dilution media

| Substrate | Composition | | pH |
|---|---|---|---|
| Phosphate Buffer | K2PO4 | 72 g·l$^{-1}$ | 7.0 |
| | KH2PO4 | 48 g·l$^{-1}$ | |
| | Distilled water | 1,000 ml | |
| Ringer solution | NaCl | 9 g·l$^{-1}$ | 7.0 |
| | Distilled water | 1,000 ml | |
| TS (Tryptone Saline) | NaCl | 8.5 g·l$^{-1}$ | 7.0 |
| | Tryptone | 1 g·l$^{-1}$ | |
| | Distilled water | 1,000 ml | |

9 ml-portions were dispensed in tubes and autoclaved at 121° C. for 15 min.

Finally, 8 of the 38 strains were selected for further studies (see Example 3): three lactobacilli isolated from cats (NCC2581, NCC2592, NCC2583), three lactobacilli from dogs (NCC2603, NCC2613, NCC2628), one bifidobacteria from cats (NCC2627) and one bifidobacteria from dogs (NCC2657).

These strains are characterized by short generation times, high counts (more than 1.0E+08 cfu/ml) during their stationary phase and stability in high numbers at 8 and 24 h post-inoculation, stability to freeze-drying followed by either storage-conditions, resistance to extreme bile-concentrations found in the duodenum (2% bile) and their low inhibition when grown in presence of up to 4% bile. Furthermore, results from DNA analyses were taken into account to select bacteria representative of the investigated diversity.

Example 3

Efficacy of Colonization in Cats

*L. reuteri* NCC2581, *L. reuteri* NCC2592, *L. rhamnosus* NCC2583 and *Bifadobacterium* sp. NCC2627 were tested in feeding trials so as to evaluate their capacity to survive the passage of the cat gastrointestinal tract.

16 cats male and female as equal as possible were subjected to 3 days of adaptation with Friskies Grand menu boeuf. The feeding protocol consisted in 7 days with "Friskies Grand Menu" and 7 days of test with "Friskies Grand Menu" containing one of the above mentioned strains: *L. reuteri* NCC2581 (diet A), *L. reuteri* NCC2592 (diet B), *L. rhamnosus* NCC2583 (diet C) and *Bifidobacterium* sp. NCC2627 (diet D). The diet assignment was the following:

| | Cats n° | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Period 1 | A | D | C | B | D | A | A | C | B | A | B | C | B | D | C | D |
| Period 2 | B | A | D | A | C | C | D | A | C | B | C | D | D | A | B | B |

The said strains were prepared in a sufficient amount and in a stable lyophilized form to apply these eight different bacteria with regard to strain-survival in the gastrointestinal tract of the tested animals. All strains were mixed with 4 g of trehalose in order to add a sufficient volume of carrier for mixing the prepared strains with the food-matrix for the animals. Bacteria strains are prepared in individual plastic tubes (1.0E+09 cfu/day) and daily added in a part of the food to be sure that total bacteria will be eaten.

Fresh fecal samples are obtained to analyze bacterial population numbers and compared with base line (without bacteria added).

Feces are collected on day 7 and 8 (base line),
day 14 and 15
day 21 and 22 (base line)
day 28 and 29.

A sterile rectal probe is used to obtain a fecal sample of at least 0.1 g. This sample is accurately weighted and 0.1 g is mixed with 10 ml of physiological solution (Ringer) containing 10% glycerol. This solution is then transferred into 1 ml cryotubes and frozen in liquid nitrogen. All samples are then stored at $-80°$ C. until analysis.

The endogenous populations of Lactobacilli, *Bacteroides*, Enterobacteriaceae, Enterococci, Bifidobacteria and *Clostridium perfringens* were counted. Bacteria were detected on selective or semi-selective media. Hundredfold serial dilutions were performed in Ringer solution containing 0.5% of cystein, from the dilutions in the range $-2$ to $-8$. Petri dishes of various selective media were inoculated and incubated (see Table below).

| Bacteria | Media | T (°C.) | Time (h) | Atmosphere |
|---|---|---|---|---|
| Enterobacteriaceae | Drigalski (Sanofi Diagnostics Pasteur, France) | 37 | 24 | Aerobic |
| *Bifidobacteria* | Eugon Tomato* | 37 | 48 | Anaerobic |
| *Lactobacilli* | MRS (Difco, MI. USA) + antibiotics** | 37 | 48 | Anaerobic |
| *Cl. perfringens* | NN Agar*** | 37 | 48 | Anaerobic |

-continued

| Bacteria | Media | T (°C.) | Time (h) | Atmosphere |
|---|---|---|---|---|
| *Bacteroides* | Schaedler Neo-Vanco (BioMerieux, Marcy-l'Etoile, France) | 37 | 48 | Anaerobic |

*Wadsworth Anaerobic Bacteriology Manual, V. Suter, D. Citron and S. Finegold Third ed.
**Phosphomycine (79.5 mg/l) + Sulfamethoxazole (0.93 mg/l) + Trimethoprime (5 mg/l)
***NN agar from Lowbury and Lilly, 1995

Results:
The bacterial counts are expressed as log base 10 and presented in Table 7.

TABLE 7

| Fecal bacterial counts in cats (mean ± Stdev, n = 8) | | | | | | | | |
|---|---|---|---|---|---|---|---|---|
| | NCC 2581 | | NCC 2592 | | NCC 2583 | | NCC 2627 | |
| | Before | During | Before | During | Before | During | Before | During |
| *Lactobacilli* | 6.38 ± 2.25 | 7.63 ± 1.23 | 6.12 ± 2.45 | 7.62 ± 1.58 | 5.31 ± 2.04 | 7.47 ± 1.23 | 6.69 ± 1.44 | 7.65 ± 1.45 |
| *Bifido-Bacteria* | 7.17 ± 1.82 | 7.64 ± 0.42 | 7.57 ± 1.68 | 6.31 ± 2.26 | 6.43 ± 2.25 | 6.80 ± 2.19 | 8.04 ± 1.03 | 6.07 ± 2.32 |
| Enterobacteriaceae. | 4.25 ± 1.71 | 4.27 ± 1.20 | 4.37 ± 1.35 | 4.58 ± 1.45 | 5.09 ± 1.50 | 4.40 ± 0.63 | 4.59 ± 1.42 | 3.64 ± 0.64 |
| *Bacteroides* | 6.05 ± 1.38 | 5.54 ± 0.49 | 5.94 ± 0.99 | 6.15 ± 1.43 | 6.19 ± 0.97 | 5.52 ± 0.46 | 6.00 ± 1.11 | 5.48 ± 0.50 |
| *C. perfr.* | 4.09 ± 1.22 | 3.84 ± 1.00 | 3.61 ± 0.57 | 3.30 ± 0.00 | 4.16 ± 1.64 | 3.34 ± 0.11 | 3.84 ± 0.89 | 3.57 ± 0.56 |

During treatment we observe an increase of the fecal counts of lactobacilli, due to the ingestions of the cited probiotic bacteria. We observe no drastic increase in count of Enterobacteriaceae reflecting that there is no damage in the intestinal ecosystem related to the use of the selected probiotics.

Example 4

Efficacy of Colonization in Dogs

*L. reuteri* NCC2603, *L. reuteri* NCC2613, *L. acidophilus* NCC2628 and *Bifidobacterium* sp. NCC2657 were tested in feeding trials so as to evaluate their capacity to survive the passage of the dog gastrointestinal tract.

10 dogs, 5 males and 5 females 4 to 7 years old, were subjected to this specific trial. The feeding protocol consisted in 5 days of adaptation with "Friskies Vitality" w/o chicory and 5 days of test with "Friskies Vitality" w/o chicory and 3 days of adaptation, 5 days of test with "Friskies Vitality" w/o chicory+bacteria: *L. reuteri* NCC2603 (diet E), *L. reuteri* NCC2613 (diet F), *L. acidophilus* NCC2628 (diet G) and *Bifidobacterium* sp. NCC2657 (diet H). The diet assignment was the following:

|  | Dog n° | | | | | | | | | |
|---|---|---|---|---|---|---|---|---|---|---|
|  | 1 | 2 | 3 | 4 | 5 | 6 | 7 | 8 | 9 | 10 |
| Period 1 | E | E | E | E | E | F | F | F | F | F |
| Period 2 | G | G | G | G | G | H | H | H | H | H |

The said strains were prepared in a sufficient amount and in a stable lyophilized form to apply these eight different bacteria with regard to strain-survival in the gastro-intestinal tract of the tested animals. All strains were mixed with 4 g of trehalose in order to add a sufficient volume of carrier for mixing the prepared strains with the food-matrix for the animals. Bacteria strains are prepared in individual plastic tubes (5.0E+09 cfu/day) and daily added in a part of the food to be sure that total bacteria will be eaten.

Fresh fecal samples are obtained to analyze bacterial population numbers and compared with base line (without bacteria added).

| Feces are collected on | day 7 and 8 (base line), day 14 and 15 day 21 and 22 (base line) day 28 and 29. |
|---|---|

A sterile rectal probe is used to obtain a fecal sample of at least 0.1 g. This sample is accurately weighted and 0.1 g is mixed with 10 ml of physiological solution (ringer) containing 10% glycerol. This solution is then transferred into 1 ml cryotubes and frozen in liquid nitrogen. All samples are then stored at −80° C. until analysis. The bacteria were counted on the same media that describe in example 3.

Results:

The bacterial counts, expressed as log base 10, are presented in Table 8.

During treatment we observe no major change in the fecal counts of lactobacilli, due to the ingestions of the selected probiotic bacteria except in the case of the strain *L. acidophilus* NCC2628. Under the tested conditions the inhibitory effect on *C. perfringens* was not significant as the basal level of *C. perfringens* were very low. We observe no drastic increase in count of Enterobacteriaceae reflecting that there is no disturbance of the intestinal ecosystem related to the use of the selected probiotics.

Example 5

Effect of Lactobacilli and their Metabolites on the Viability of *Giardia intestinalis*

We studied the effect of culture filtrate supernatants of Lactobacilli strains isolated from cats and dogs.

Material and Methods

Bacterial Strains and Cultures:

Micro-organisms belonging to the genus *Lactobacillus* were from the Nestle Culture Collection. Bacteria were grown in MTYI medium. Supernatants containing metabolites of lactobacilli were neutralized at pH 6 and filter sterilized.

Controls were performed by acidifying MTYI medium with lactic acid to the same pH than the one of the bacterial cultures. Afterwards, pH was adjusted to pH 6 with 0.1 N NaOH. Origin of the strain under study and pH of supernatants and controls are shown in table 9.

TABLE 9

| Strain | Origin | pH supernatant | pH control |
|---|---|---|---|
| *L. reuteri* NCC2581 | Cat | 6.63 | 6.63 |
| *L. rhamnosus* NCC2583 | Cat | 6.50 | 5.97 |
| *L. reuteri* NCC2592 | Cat | 6.04 | 5.98 |
| *L. reuteri* NCC2603 | Dog | 6.04 | 5.99 |
| *L. reuteri* NCC2613 | Dog | 6.07 | 5.95 |
| *L. acidophilus* NCC2628 | Dog | 6.01 | 5.93 |

Parasites:

*Giardia intestinalis* strain WB (ATCC 30957) was purchased to American Type Culture Collection (Rockville, USA). Trophozoites were grown in Keister's modified TYI-S-33 medium containing per liter: casein digest (Difco), 20 g; yeast extract (BBL), 10 g; dextrose (Merck), 10 g; bovine bile (Difco), 0.75 g; NaCl (Merck), 2 g; L-cystein.HCl (Sigma), 2 g; ascorbic acid sodium salt (Fluka), 0.2 g; $K_2HPO_4$ (Merck), 0.6 g; ferric ammonium citrate (Sigma), 22.8 mg; adult bovine serum (Sigma), 100 ml; penicillin/streptomycine (Gibco, 1000 IU/ml, 1000 µg/ml), 15 ml. pH was adjusted to 6.9 with NaOH 5N prior to filter sterilization (0.22 µm pore size).

TABLE 8

Fecal bacterial counts in dogs (mean ± Stdev, n = 5)

|  | NCC 2603 | | N0CC 2613 | | NCC 2628 | | NCC 2657 | |
|---|---|---|---|---|---|---|---|---|
|  | Before | During | Before | During | Before | During | Before | During |
| Lactobacilli | 5.25 ± 1.34 | 3.92 ± 1.05 | 4.00 ± 1.56 | 3.40 ± 0.21 | 7.93 ± 1.75 | 8.30 ± 0.99 | 6.47 ± 1.27 | 7.00 ± 1.35 |
| Bifdobac. | 7.32 ± 2.06 | 4.48 ± 2.64 | 6.09 ± 2.10 | 4.55 ± 2.79 | 7.70 ± 2.57 | 7.20 f 1.88 | 5.72 ± 2.51 | 6.78 ± 2.39 |
| Enterobact. | 4.10 ± 0.89 | 4.62 ± 0.61 | 3.62 ± 0.72 | 4.39 ± 0.94 | 4.58 ± 1.54 | 4.04 ± 0.76 | 4.51 ± 1.51 | 4.85 ± 1.45 |
| Bacteroides | 7.82 ± 053 | 6.70 ± 1.25 | 6.92- ± 1.37 | 6.69 ± 1.19 | 7.88 ± 1.13 | 7.53 ± 0.61 | 7.92 ± 0.63 | 7.66 ± 0.86 |
| C. perfr. | 3.70 ± 0.89 | 3.84 ± 0.87 | 3.50 ± 0.45 | 3.30. ± 0 | 3.70 ± 0.62 | 3.30 ± 0 | 3.93 ± 1.25 | 3.70 ± 0.89 |

Parasites were cultured in polystyrene tissue culture flasks (LUX, Miles Laboratories, Inc. Naperville, Ill. 60540) filled with 40 ml of culture medium. Subcultures were performed by discarding supernatant with non attached parasites, adding 5 ml of ice-cold culture medium, incubating in an ice bath for 10 min to detach adherent trophozoites and inoculating 0.2 ml of the resulting suspension into fresh medium. Incubations were performed at 37° C. in the dark.

Proliferation assays: Two hundred microliters of trophozoite suspensions ($1.4 \times 10^5$ parasites/ml) were mixed with 100 µl of supernatants or controls and 1 µCi of $^3$H thymidine was added. Samples were incubated at 37° C. for 24 hours in 96-well tissue culture plates (Nunc Brand Products). Then, parasites were harvested and thymidine incorporation was evaluated.

Results

Thymidine incorporation is shown in Table 10. The strain NCC 2628 isolated from a dog produced a strong inhibition of the proliferation of WB strain (91%). Other strains studied did not inhibit trophozoite growth.

TABLE 10

Effect of culture filtrate supernatants on proliferation of *Giardia intestinalis* strain

| Strain | Proliferation *Giardia intestinalis* In CPM |
|---|---|
| *L. reuteri* NCC 2581 | 1720 |
| Control | 2000 |
| *L. rhamnosus* NCC 2583 | 2500 |
| Control | 1720 |
| *L. reuteri* NCC 2592 | 1800 |
| Control | 1970 |
| *L. reuteri* NCC 2603 | 2100 |
| Control | 1900 |
| *L. reuteri* NCC 2613 | 2510 |
| Control | 1950 |
| *L. acidophilus* NCC 2628 | 150 |
| Control | 1610 |
| MTYI | 1870 |

In this experiment it could be demonstrated that functional metabolites produced during growth of *L. acidophilus* NCC 2628 have a very strong inhibitory effect on the growth of *Giardia intestinalis*.

Examples 6 to 8

Inhibitory Effects of *lactobacillus* Strains According to the Invention on Intestinal Pathogenic Bacteria To identify strains with strong antagonistic properties against small intestinal pathogens, co-cultivation experiments were performed in a model system simulating canine small intestinal conditions (pH, bile composition and concentration, mucin, pancreatin). Simulated canine small intestinal juice contained reconstituted canine bile (0.345 g/l taurochenodeoxycholate, Sigma, Germany; 0.7 g/l taurodeoxycholate, Sigma, Germany; 3.04 g/l taurocholate, Sigma, Germany; 0.006 g/l cholate Fluka, Switzerland), porcine mucine (1.9 g/l Sigma, Germany), porcine pancreatin (2.42 g/l, Sigma, Germany) and electrolyte solution (5 g/l NaCl, 0.6 g/l KCl, 0.25 g/l CaCl$_2$, all Merck, Germany). The pH of the juice was adjusted to pH 6.5±0.5 with 0.1 N NaOH.

Strains and Cultivation Conditions

Small Intestinal Pathogens

Four potentially pathogenic strains were selected: *S. typhimurium* SL1344, *E. coli* ETEC O8:H9 and *E. coli* O149:K$_{88}$ (pathogenic canine isolate) and a clinical isolate of *Sh. dysenteriae* (human origin, kindly provided by Centre Hospitalier Universitaire Vaudoise—CHUV Lausanne, Switzerland). With the exception of *S. typhimurium* SL1344 propagated in Luria Bertani broth (Difco, USA), all enterobacteriaceae were grown in Brain Heart Infusion broth (Difco, USA) at 37° C. under shaking (240 rpm).

Lactic Acid Bacteria

A wide range of lactobacilli of canine and feline origin including *L. acidophilus* NCC2628 (CNCM I-2453), *L. rhamnosus* NCC2583 (CNCM 1-2449), *L. reuteri* NCC2581 (CNCM I-2448), *L. reuteri* NCC2592 (CNCM I-2450) were selected from the Nestle Culture Collection (NCC, Nestec, Switzerland) and screened in the canine small intestinal model for survival, physiological activity and inhibitory effects on above mentioned small intestinal pathogens. Lactobacilli were cultured anaerobically (anaerocult, Oxoid, England) in Man Rogosa Sharp broth (Difco, USA) at 37° C.

Determination of Viable Cell Counts

Samples were diluted in sterile phosphate buffer (NaH$_2$PO$_4$, pH 7, 0.2 M) and surface plated of 10-fold dilutions on agar plates: MRS agar (Difco, USA) for lactobacilli, *Salmonella-Shigella* agar (Oxoid, England) for *S. typhimurium* and *Sh. dysenteriae*, and Sorbitol Mac Conkey agar (Oxoid, England) for *E. coli*. Agar plates were incubated 48 hours at 37° C. anaerobically for lactobacilli, and 24 hours at 37° C. for enterobacteriaceae. For co-cultivation trials, the growth of enterobacteriacea on MRS agar was inhibited by addition of polymixin (Oxoid, England).

Co-Cultivation Experiments Between Lactic Acid Bacteria (LAB) and Pathogens

Co-cultivation experiments with potential probiotic LAB and pathogenic strains were performed at 37° C. in 20 ml (Falcon tubes) simulated canine small intestinal juice enriched with different carbon sources (sugar, pet food) to favor metabolic activity of the cultures. LAB were inoculated at 10E+08 cfu/ml, pathogens at 10E+02 cfu/ml, 10E+04 cfu/ml and 10E+06 cfu/ml. Samples were taken at different time points up to 8 hours and viable cell counts were determined by surface plating of 10-fold dilutions on respective media.

Co-cultivation trials were performed under different conditions including enrichment of simulated canine small intestinal juice with dextrose (5 g/l) and different concentrations of commercially available extruded dry pet food (5, 25 or 100 g/l; Friskies ALPO Complete, USA). The latter was homogenized (Stomacher Lab Blender) and suspended in electrolyte solution. All experiments were performed in duplicate.

Example 6

Co-cultivation experiments between four lactobacilli and the four potentially pathogenic strains *E. coli* ETEC O8:H9, *E. coli* O149:K88, *S. typhimurium* SL1344 and *Sh. dysenteriae* were performed in simulated canine duodenal juice enriched with 5 g/l dextrose (Difco). Lactobacilli were inoculated at 10E+08 cfu/ml and the Gram negative indicator strains at 10E+02 cfu/ml. Results are compiled in Table 11.

TABLE 11

Co-cultivation between LAB and potentially pathogenic bacteria in simulated canine small intestinal juice enriched with dextrose

| | Pathogen | | | |
|---|---|---|---|---|
| PROBIOTIC | *E. coli* ETEC O8:H9 | *E. coli* O149:K88 | *S. typhimurium* SL1344 | *Sh. dysenteriae* |
| *L. acidophilus* NCC2628 (CNCM I-2453) | +++ | +++ | +++ | +++ |

TABLE 11-continued

Co-cultivation between LAB and potentially pathogenic bacteria in simulated canine small intestinal juice enriched with dextrose

| PROBIOTIC | Pathogen | | | |
|---|---|---|---|---|
| | E. coli ETEC O8:H9 | E. coli O149:K88 | S. typhimurium SL1344 | Sh. dysenteriae |
| L. rhamnosus NCC2583 (CNCM I-2449) | +++ | +++ | +++ | +++ |
| L. reuteri NCC2581 (CNCM I-2448) | No inhibition | ++ | No inhibition | +++ |
| L. reuteri NCC2592 (I-2450) | No inhibition | ++ | No inhibition | + |

+ Inhibition of growth
++ Inhibition of growth and partial inactivation
+++ Inhibition of growth and complete inactivation All four investigated lactobacilli demonstrated antimicrobial activity but only L. acidophilus NCC2628 (CNCM I-2453) and L. rhamnosus NCC2583 (CNCM I-2449) demonstrated high activity against all tested pathogens. Both strains were not only able to inhibit the growth, but were also able to completely inactivate the pathogens contained in the test system (no remaining viable cells).

Example 7

Co-cultivation experiments were performed between lactobacilli [(L. acidophilus NCC2628 (CNCM I-2453), L. rhamnosus NCC2583 (CNCM I-2449) and S. typhimurium SL1344 in simulated canine duodenal juice enriched with commercially available extruded dry pet food (5, 25 or 100 g/l; Friskies ALPO Complete, USA). Lactobacilli were inoculated at 10E+08 cfu/ml and the Gram negative indicator strains at 10E+02 cfu/ml. Results are compiled in Table 12.

TABLE 12

Co-cultivation between LAB and potentially pathogenic bacteria in simulated canine small intestinal juice enriched with dry pet food

| PROBIOTIC | Pathogen | |
|---|---|---|
| | Enrichment with pet food | S. typhimurium SL1344 |
| L. acidophilus NCC2628 (CNCM I-2453) | 5 g/l | +++ |
| | 25 g/l | +++ |
| | 100 g/l | +++ |
| L. rhamnosus NCC2583 (CNCM 1-2449) | 5 g/l | No inhibition |
| | 25 g/l | + |
| | 100 g/l | ++ |

+ Inhibition of growth
++ Inhibition of growth and partial inactivation
+++ Inhibition of growth and complete inactivation Results demonstrate the high potential of especially L. acidophilus NCC2628 (CNCM I-2453) to inhibit the growth and even to inactivate completely small intestinal pathogens under very practical conditions such as in a mix of simulated small intestinal juice and pet food. The antimicrobial activity of L. acidophilus NCC2628 was very high even at low levels of enrichment with commercial pet food serving as a source of fermentable sugars for the organism. In contrast this observation made for L. rhamnosus NCC2583 (CNCM I-2449) the effectiveness of L. rhamnosus NCC2583 (CNCM I-2449) was depending on the level of enrichment with pet food in that way that an increasing antimicrobial activity was observed with increasing amounts of pet food added to the test system.

Example 8

Co-cultivation experiments with L. acidophilus NCC2628 (CNCM I-2453) and different inoculation levels of S. typhimurium SL1344 were performed in simulated canine duodenal juice enriched with dextrose (5 g/l, Difco). L. acidophilus NCC2628 (CNCM I-2453) was inoculated at 10E+08 cfu/ml, S. typhimurium SL1344 was inoculated at 10E+02 cfu/ml, 10E+04 cfu/ml and 10E+06 cfu/ml. Results are compiled in Table 13.

TABLE 13

Co-cultivation of L. acidophilus NCC2628 (CNCM 1-2453) and different inoculation levels of S. typhimurium SL1344

| PROBIOTIC | Pathogen | |
|---|---|---|
| | Inoculation level of the pathogen | S. typhimurium SL1344 |
| L. acidophilus NCC2628 (CNCM I-2453) | 10E+02 cfu/ml | +++ |
| | 10E+04 cfu/ml | +++ |
| | 10E+06 cfu/ml | +++ |

+ Inhibition of growth
++ Inhibition of growth and partial inactivation
+++ Inhibition of growth and complete inactivation The antimicrobial activity of L. acidophilus NCC2628 (CNCM I-2453) was sufficiently high to completely inactivate even high initial concentration of S. typhimurium SL1344.

Example 9

In-Vivo Immune Stimulation in Dogs

The immune stimulating potential for pet-isolated strains of probiotics was tested in a clinical trial using the L. acidophilus NCC 2628 strain.

Methods:

Canine Peripheral Blood Mononuclear Cells (PBMC) Proliferation Upon Stimulation with Different Mitogens:

20 dogs 4 to 7 years old were subjected to this trial. The feeding protocol consisted in one week of adaptation with "Friskies Vitality" w/o chicory and 4 weeks of test with "Friskies Vitality" w/o chicory+L. acidophilus NCC2628 bacteria.

L. acidophilus NCC2628 was prepared in a sufficient amount and in a stable lyophilized form with, regard to strain survival in the gastro-intestinal tract of the tested animals. Bacteria were mixed with 4 g of trehalose in order to add a sufficient volume of carrier for mixing the prepared bacteria with the food-matrix for the animals. Bacteria were prepared in individual plastic tubes (5.0E+09 cfu/day) and daily added in a part of the food to be sure that total bacteria will be eaten.

Blood was collected from the dogs after the four weeks of probiotic administration. The blood was fractionated through a Vaccutainer™ column (Becton Dickinson, Mountain View, Calif.). PBMC were recovered according to the manufacturer's recommendations.

Cells were stimulated with different mitogens or phorbol esters that induce a strong proliferation of T cells (concanavalin A (conA), Phytohemaglutinin (PHA)), of B cells (Pokeweed mitogen (PWM)), and of all cells (Phorbol-Myristate-Acetate/Ionomycine (PMAA/Iono)). $10^5$ cells per well were incubated with mitogens or the phorbol esters (the respective doses are indicated in the FIG. 1) in a final volume of 200 µl of RPMI-1640 culture medium supplemented with 10% fetal calf serum and antibiotics in 96-well flat-bottom culture plates (Nunc).

Cells were maintained in humidified 5% $CO_2$ atmosphere at 37° C. for 48 h. The cells were pulse-labelled with 1 µCi of [$^{31}$H]thymidine (Amersham Pharmacia Biotech, Switzerland) for a further 18 h. The cells were then harvested on nitrocellulose filters (Packard) and bound [$^3$H]thymidine was measured by scintillation counting (TopCount; Packard, Switzerland). Cell proliferation was calculated as the mean (counts per minute (c.p.m) (±SD) from triplicates.

Results:

FIG. 1: There was a clear increase in cell proliferation in response to all mitogens in the group of dog fed with *L acidophilus* NCC2628 compared with the control group. This increase was significant in cultures stimulated with the phorbol esters PMA+ionomycin. This data shows that lymphoid cells from probiotic-fed dogs were more reactive upon activation in vitro and suggests that the immune system of probiotic-fed dogs has been stimulated.

Example 10

In Vitro Modulation of Immune Functions by Pet-Isolated *lactobacillus* Strains

An in-vitro screening of the different pet-isolated *lactobacillus* strains described above was setup to determine their immune modulation potential. To this end, we measured their ability to induce pro-inflammatory cytokines (IL-12, IFNγ) and/or anti-inflammatory cytokines (IL-10, TGF-β) (Anand A. C., Adya C. M. 1999, *Trop. Gastroenterol.;* 20(3):97-106; Spellberg B., Edwards J. E. Jr 2001, *Clin. Infect. Dis.;* 32(1): 76-102.). This aimed at selecting potential candidate strains for strong anti-pathogenic or anti-cancer immune functions as well as antagonistic functions against canine intestinal pathologies such as allergy and inflammation (Inflammatory bowel diseases). Additional cultures were set up with medium alone (negative control), with *Enterococcus faecium* strain SF68 (NCIMB 10415, Cerbios-Pharma, Switzerland) and with a human *lactobacillus* isolate ST11 (NCC 2461, CNCM I-2116) (positive control).

Method:

Cytokine Profiles Induced by Different Probiotic Strains in Canine Leukocytes:

Blood from normal adult dogs was treated 5 min at room temperature with ACK lysing buffer (150 mM of $NH_4Cl$, 1 mM of $KHCO_3$, and 0.1 mM of $Na_2EDTA$ in $H_2O$, pH=7.4). The leukocytes were washed twice with RPMI medium (without antibiotics) and seeded at 2·10$^6$ cell/ml into 24-well tissue culture plates 1 ml of a bacterial suspension (described below) containing 10$^6$ CFU was added to each well.

For control treatment, medium alone was added to the leukocytes. The samples were incubated 18 h at 37° C. and 5% $CO_2$. Subsequently, leukocytes were collected, washed in PBS and centrifuged. The cell pellet was lysed with 500 µl of Trizol reagent (Gibco BRL). RNA was extracted from cellular lysates using the Nucleospin RNA kit (Macherey-Nagel). RT-PCR for canine cytokine amplifications were performed using the AB gene kit (Merck). The primer references (all produced by Microsynth) are indicated below. Densitometric analysis of the PCR-bands revealed in the ethidium bromide-stained agarsose gels was performed using the NM Image software. All bands were normalised with the respective β-actin PCR-product band obtained with each sample (internal control), and the results are expressed as arbitrary units reflecting the pixel densities of each cytokine PCR-product band (FIG. 2).

Preparation of the bacteria: the different strains of lactobacilli were grown in MRS medium for approximately 8 h until they reached identical density. The bacteria were diluted in RPMI medium without antibiotics to final concentrations of 10$^6$ CFU/ml.

Primers used for cytokine RT-PCRs:

| Cyokines | References |
|---|---|
| IL-12p40 | Biittner M., et al. 1998. Cytokine; 10(4): 241-248. |
| IFNγ | Biittner M., et al. 1998. Cytokine; 10(4): 241-248. |
| TGFβ1 | Grone A., et al. 1998. Vet. Immunol. Immunopathol.; 65: 11-27. |
| IL-10 | Pirelli E., et al., 1999, Vet. Immunol. Immunopathol.; 69: 121-126. |

Results:

FIG. 2: The data show that cytokine profiles induced by lactobacilli are strain-dependent. For example, the strain NCC2628 induced high levels of IL-10 and TGF-β, highlighting the potential for this particular strain for the immune modulation of inflammatory disorders such as allergy and inflammatory bowel diseases. In contrast, the strain NCC2583 induced strong levels of IFNγ and IL-12, which makes this strain a good candidate for anti-pathogenic or anti-cancer activity.

Example 11

Three dried pet foods are used in the study. These will be referred to as "A", "B" and "C". Pet Food A is a nutritionally complete dried pet food, available under the brand name ALPO (ALPO is a registered trade mark of SOCETE DES PRODUITS NESTLE S.A. of Switzerland).

Pet Food B is the same nutritionally complete dried pet food as Pet Food A, but is supplemented with a powdered mixture of selected probiotic micro-organisms fed from a sachet. The mixture comprises substantially equal amounts of *L. acidophilus* NCC2628 and *bifidobacterium* sp. NCC2657. It is sprinkled over the food at each meal serving, the dosage supplied being about 1.0138 cfu/day.

Pet Food C is a nutritionally complete dried pet food which is substantially identical to Pet Food A but which contains 1.2% by weight of a dried supernatant of a culture of *Enterococcus faecium* SF68 (NCIMB 10415).

30 dogs are used in the study. The dogs are pre-fed for 8 weeks using Pet Food A. The dogs are then divided into 3 groups of 10 dogs each, designated groups A, B and C and fed the correspondingly-named diets for 8 weeks:

The dogs have free access to water and are fed once a day. The prevalence of dandruff in the coat is determined by a 30 member evaluation panel at commencement and then at 7 weeks later.

The dogs are groomed prior to evaluation by the panel and the panel members do not compare notes during the evaluation.

In this evaluation the dogs are presented to each of the individual panelists in 20 different pairings. The panelists are asked to indicate on a their scoresheets which dog of the pair presented displays (1) less dandruff (2) higher coat gloss and (3) less coat odour.

The overall coat condition of all dogs is visually and tactilely good as can be expected of normal, healthy dogs. However, the dogs which are fed diet C are found to have noticeably less dandruff than those fed on control diet A. Those fed on diet B have noticeably glossier coat and exhibit less noticeable coat odour than those on A. These characteristics are found not to differ significantly statistically when compared with the dogs in group B.

Example 12

A feed mixture is made up of about 58% by weight of corn, about 6% by weight of corn gluten, about 23% by weight of meat and meal, salts, vitamins and minerals making up the remainder.

The feed mixture is fed into a preconditioner and moistened. To this mixture is added a powder containing a mixture of the following *Lactobacillus* strains: *Lactobacillus rhamnosus* NCC2583 (CNCM I-2449), *Lactobacillus acidophilus* NCC2628 (CNCM I-2453) and *Enterococcus faecium* SF68 (NCIIVIB 10415). The powder is substantially homogeneously dispersed throughout the mixture. This moistened feed mix is then fed into an extruder-cooker and gelatinised. The gelatinised matrix leaving the extruder is forced through a die and extruded. The extrudate is cut into pieces suitable for feeding to dogs, dried at about 110° C. for about 20 minutes, and cooled to form pellets. The extrudate pieces are checked for bacterial activity of the added strains. None is detected.

Example 13

24 dogs are used in this study. They include younger and older dogs, the latter being from 8 to 12 years in age. The older dogs selected, exhibit external signs of joint inflammation commensurate with their ages and appear to experience some difficulty in moving at times. Certain movements appear to be painful. These symptoms are often observed in older dogs and are believed to relate to arthritic condition.

Three dried pet foods are used in the study, designated A, B and C. Pet Food A is a nutritionally complete dried pet food (ALPO Beefy Dinner). This is the control food.

All 24 members of the selected are pre-fed for 8 weeks using Pet Food A. The dogs are then divided into 3 groups, A, B and C each having 8 dogs and the same proportion of younger and older within. Each group is then fed the following respective diets for 8 weeks:

| Group - | Pet Food |
| --- | --- |
| A | A |
| B | B |
| C | C |

Pet Food B is a nutritionally complete dried pet food which is substantially identical to Pet Food A but which contains has a coating making up 2% of its weight, the coating comprising the micro-organisms of *Enterococcus faecium* SF68 (NCIMB 10415). The quantity of food fed daily to each dog is calculated according to individual body mass, so that the dosage of 1.0E+09 cfu/day.

Diet C comprises the extruded kibbles produced in example 12 above. The quantity of food fed daily to each dog is calculated according to individual body mass, so that the micro-organism dosage is 1.0E+11 cfu/day.

The dogs have free access to water and are fed once a day. An activity meter is attached to the collar of each dog and measurements are taken daily. The dogs are also visually evaluated for activity by kennel staff.

The condition of all dogs is visually and tactilely good as can be expected of normal, healthy dogs. However, the dogs in the groups that receive pet food diets B and C are noticeably more active than their counterparts on diet A. Meter readings support these observations.

Further, the elderly dogs in groups B and C, after being fed diets B and C for the trial period, appear to exhibit fewer external signs of local joint inflammation. Further, the dogs appear to experience lower levels of pain on physical movement and move more freely than before. It can be concluded that diets B and C appear to provide relief with respect to certain signs of ageing and improve the motility of older pets.

Example 14

Dry Cat Food

A feed mixture is made up of about 58% by weight of corn, about 6% by weight of corn gluten, about 23% by weight of chicken meal, salts, vitamins and minerals making up the remainder.

The feed mixture is fed into a preconditioner and moistened. The moistened feed is then fed into an extruder-cooker and gelatinised. The gelatinised matrix leaving the extruder is forced through a die and extruded. The extrudate is cut into pieces suitable for feeding to cats, dried at about 110° C. for about 20 minutes, and cooled to form pellets. At this point, a lyophilized powder of one or more strains of the following *Lactobacillus* species is provided for application to the pellets: *Lactobacillus rhamnosus* NCC2583 (CNCM I-2449), *Lactobacillus acidophilus* NCC2628 (CNCM I-2453) or *Enterococcus faecium* SF68 (NCIMB 10415). Sufficient powder is thus provided so that the corresponding dietary intake amount for the cat is from about 1.0E+07-1.0E+9 cfu/day. Some of the powder is mixed into a first mass of pellets and bagged. A second quantity of the powder is measured out and mixed with a lipid carrier which is then sprayed on to a second mass of pellets. The pellets are bagged after the coating has dried sufficiently at 50-60° C. for some minutes.

Example 15

Canned Pet Food and Supplement

A mixture is prepared from 73% of poultry carcass, pig lungs and beef liver (ground), 16% of wheat flour, 2% of dyes, vitamins, and inorganic salts. This mixture is emulsified at 12° C. and extruded in the form of a pudding which is then cooked at a temperature of 90° C. It is cooled to 30° C. and cut in chunks. 45% of these chunks are mixed with 55% of a sauce prepared from 98% of water, 1% of dye and 1% of guar gum. Tinplate cans are filled and sterilized at 125° C. for 40 min. As a probiotic supplement to be mixed with the pet food before serving, additional packaging in sachet form with strains of the following *Lactobacillus* species are provided *Lactobacillus rhamnosus* NCC2583 (CNCM I-2449), *Lactobacillus acidophilus* NCC2628 (CNCM I-2453) or *Enterococcus faecium* SF68 (NCIMB 10415). The corresponding amount for the pet is from about $106\text{-}10^{12}$ cfu/day, depending on whether a cat or a dog and on physical factors such as body mass. This is supplied as a supplement with removably attached to the can, together with feeding directions.

It should be understood that various changes and modifications to the presently preferred embodiments described herein will be apparent to those skilled in the art. Such changes and modifications can be made without departing from the spirit and scope of the present subject matter and The invention is claimed as follows:

1. A method for producing a pet food, the method comprising:
   providing a probiotic;
   exposing the probiotic to a gastric juice;
   providing a model of a pet small intestine;
   introducing the probiotic and a pathogen into the model;
   measuring the amount of an anti-pathogenic metabolite produced by the probiotic; and
   adding the provided probiotic to an ingestible composition for pets in an amount sufficient to produce an effective anti-pathogenic metabolite,
   wherein the probiotic is a bacterial strain selected from the group consisting of *Lactobacillus acidophilus* NCC 2766 (CNCM I-3848), *Lactobacillus acidophilus* NCC 2775 (CNCM I-3851), *Lactobacillus acidophilus* NCC 2628 (CNCM I-2453), *Lactobacillus johnsonii* NCC 2777 (CNCM I-3852), *Lactobacillus johnsonii* NCC 2767 (CNCM I-3849), *Lactobacillus johnsonii* NCC 2774 (CNCM I-3850), and *Lactobacillus salivarius* NCC 2586 (CNCM I-3847).

2. The method of claim 1, wherein the pet is a canine.

3. The method of claim 1, wherein the pet food is dog food.

4. The method of claim 1, wherein the provided probiotic produces an anti-pathogenic metabolite that lowers the pH of the gastrointestinal tract locally to a range of from about 4.5 to about 5.5.

5. The method of claim 1, wherein the provided probiotic produces an anti-pathogenic metabolite that inhibits the growth of a pathogen present in the gastrointestinal tract, the pathogen selected from the group consisting of enterotoxigenic *Escherichia coli, Escherichia coli, Salmonella typhimurium, Shigella dysenteriae* and combinations thereof.

6. The method of claim 1, wherein the pathogen introduced into the model is selected from the group consisting of enterotoxigenic *Escherichia coli, Escherichia coli, Salmonella typhimurium, Shigella dyvsenteriae* and combinations thereof.

7. The method of claim 1, wherein the anti-pathogenic metabolite produced by the probiotic is selected from the group consisting of lactic acid, acetic acid, citric acid, pyruvic acid, hydrogen peroxide, and combinations thereof.

8. The method of claim 1, wherein the provided probiotic produces lactic acid in an amount of from about 10 mM to about 90 mM.

9. The method of claim 1, wherein the provided probiotic produces hydrogen peroxide in an amount of from about 0.1 mM to about 4.5 mM.

10. The method of claim 1, wherein the provided probiotic is capable of surviving in a pH 2.6 environment for at least 10 minutes.

11. The method of claim 1, wherein the provided probiotic is capable of surviving in a pH 3.4 environment for at least 60 minutes.

12. The method of claim 1, wherein the provided probiotic is obtained from a fecal sample of a dog or a cat.

* * * * *